US009951039B2

(12) United States Patent
Wong et al.

(10) Patent No.: US 9,951,039 B2
(45) Date of Patent: Apr. 24, 2018

(54) PYRIMIDINES FOR TREATMENT OF BACTERIAL INFECTIONS

(71) Applicants: The Hong Kong Polytechnic University, Hong Kong (CN); The Royal Institution for the Advancement of Learning / McGill University, Montreal (CA)

(72) Inventors: Kwok-yin Wong, Hong Kong (CN); Tak-Hang Chan, Hong Kong (CN); Kin-Fai Chan, Hong Kong (CN)

(73) Assignees: THE HONG KONG POLYTECHNIC UNIVERSITY (CN); THE ROYAL INSTITUTION FOR THE ADVANCEMENT OF LEARNING/MCGILL UNIVERSITY (CA)

( * ) Notice: Subject to any disclaimer, the term of this patent is extended or adjusted under 35 U.S.C. 154(b) by 0 days.

(21) Appl. No.: 15/279,686

(22) Filed: Sep. 29, 2016

(65) Prior Publication Data

US 2017/0291887 A1 Oct. 12, 2017

Related U.S. Application Data

(60) Provisional application No. 62/319,894, filed on Apr. 8, 2016.

(51) Int. Cl.
C07D 401/04 (2006.01)
(52) U.S. Cl.
CPC .................. C07D 401/04 (2013.01)
(58) Field of Classification Search
USPC ........................ 514/218, 247, 277
See application file for complete search history.

(56) References Cited

U.S. PATENT DOCUMENTS 8,618,288 B2 * 12/2013 Dvorak ................ C07D 487/04
544/242

OTHER PUBLICATIONS

Klevens, R. et al., Invasive methicillin-resistant *Staphylococcus aureus* infections in the united states. JAMA 2007, 298 (15), 1763-1771.
CDC. Antibiotic Resistance Threats in the United States, 2013, http://www.cdc.gov/drugresistance/pdf/ar-threats-2013-508.pdf.
Lock, el at, Cell-division inhibitors: new insights for future antibiotics. Nat. Rev. Drug Discov. 2008, 7 (4), 324-338.
Sass, P. et al., Bacterial cell division as a target for new antibiotics. Curr. Opin. Microbiol. 2013, 16 (5), 522-530.
Foss, M. H. et al., Chemical-Biological Studies of Subcellular Organization in Bacteria. Biochemistry 2011, 50 (36), 7719-7734.
Schaffner-Barbero, C. et al., Targeting the Assembly of Bacterial Cell Division Protein FtsZ with Small Molecules. ACS Chem. Biol. 2012, 7 (2), 269-277.
Ma, S. et al., The Development of FtsZ Inhibitors as Potential Antibacterial Agents. ChemMedChem 2012, 7 (7), 1161-1172.
Ojima, I. et al., Drug discovery targeting cell division proteins, microtubules and FtsZ. Bioorganic Med. Chem. 2014, 22 (18), 5060-5077.
Hurley, K. A. et al., Targeting the bacterial division protein FtsZ. J. Med. Chem. 2016, 59 (15), 6975-6998.
Li, Y. et al., FtsZ Protofilaments Use a Hinge-Opening Mechanism for Constrictive Force Generation. Science 2013, 341 (6144), 392-395.
Matsui, T. et al., Structural Change in FtsZ Induced by Intermolecular Interactions between Bound GTP and the T7 Loop. J. Biol. Chem. 2014. 289 (6), 3501-3509.
Haydon, D. J. et al., An inhibitor of FtsZ with potent and selective anti-staphylococcal activity. Science 2008, 321 (5896), 1673-1675.
Haydon, D. J. et al., Creating an Antibacterial with in Vivo Efficacy: Synthesis and Characterization of Potent Inhibitors of the Bacterial Cell Division Protein FtsZ with Improved Pharmaceutical Properties. J. Med. Chem. 2010, 53 (10), 3927-3936.
Qiang, S. et al., Synthesis and Biological Evaluation of Novel FtsZ-targeted 3-arylalkoxy-2,6-difluorobenzamides as Potential Antimicrobial Agents. Chem. Biol. Drug Des. 2016, 87, 257-264.
Kaul, M. et al., An FtsZ-Targeting Prodrug with Oral Antistaphylococcal Efficacy In Vivo. Antimicrob. Agents Chemother. 2013, 57 (12), 5860-5869.
Kaul, M. et al., Pharmacokinetics and in vivo antistaphylococcal efficacy of TXY541, a 1-methylpiperidine-4-carboxamide prodrug of PC190723. Biochem. Pharmacol. 2013, 86 (12), 1699-1707.
Kate, M. et al., TXA709, an FtsZ-Targeting Benzamide Prodrug with Improved Pharmacokinetics and Enhanced In Vivo Efficacy against Methicillin-Resistant *Staphylococcus aureus*. Antimicrob. Agents Chemother. 2015, 59 (8), 4845-4855.
Lepak, A. J. et al., In Vivo Pharmacodynamic Evaluation of an FtsZ Inhibitor, TXA-709, and Its Active Metabolite, TXA-707, in a Murine Neutropenic Thigh Infection Model. Antimicrob. Agents Chemother. 2015, 59 (10), 6568-6574.

(Continued)

*Primary Examiner* — Pancham Bakshi
(74) *Attorney, Agent, or Firm* — Law Offices of Albert Wai-Kit Chan, PLLC

(57) ABSTRACT

Filamenting temperature-sensitive mutant Z (FtsZ) protein plays a crucial role in the bacterial cell division machinery and is a validated drug target for antibacterial agents. The present invention relates to FtsZ-interacting compounds that possess a 2,4,6-trisubstituted pyrimidine scaffold. Some of these compounds possess potent anti-staphylococcal properties and potent antibacterial activities against clinically isolated MRSA strains. Compounds have been identified to exhibit low spontaneous frequency of resistance, low toxicity as well as the ability to rescue *G. mellonella* larvae infected with lethal dose of the MRSA ATCC 43300 strain. Characterization by saturation transfer difference NMR, light scattering assay and GTPase hydrolysis assay with purified *S. aureus* FtsZ protein verified the interaction of 2,4,6-trisubstituted pyrimidine with the FtsZ protein, further confirmed by observations of iconic filamentous cell phenotype and mislocalization of the Z-ring formation. Taken together, these pyrimidine derivatives have the potential as effective treatment of staphylococcal infections.

20 Claims, 19 Drawing Sheets

(56) References Cited

OTHER PUBLICATIONS

Stokes, N. R. et al., An Improved Small-Molecule Inhibitor of FtsZ with Superior In Vitro Potency, Drug-Like Properties, and In Vivo Efficacy. Antimicrob. Agents Chemother. 2013, 57 (1), 317-325.

Matsui, T. et al., Structural reorganization of the bacterial cell-division protein FtsZ from *Staphylococcus aureus*. Acta Cryst. D 2012, 68, 1175-1188.

Tan, C. M. et al., Restoring Methicillin-Resistant *Staphylococcus aureus* Susceptibility to beta-Lactam Antibiotics. Sci. Transl. Med. 2012, 4 (126), 126ra35.

Kaul, M. et al., A Bactericidal Guanidinomethyl Biaryl That Alters the Dynamics of Bacterial FtsZ Polymerization. J. Med. Chem. 2012, 55, 10160-10176.

Plaza, A. et al., Chrysophaentins A-H, Antibacterial Bisdiarylbuterie Macrocycles That Inhibit the Bacterial Cell Division Protein FtsZ. J. Am. Chem. Soc. 2010, 132 (26), 9069-9077.

Marcelo, F. et al., Interactions of Bacterial Cell Division Protein FtsZ with C8-Substituted Guanine Nucleotide Inhibitors. A Combined NMR, Biochemical and Molecular Modeling Perspective. J. Am. Chem. Soc. 2013, 135 (44), 16418-16428.

Huecas, S. et al., Beyond a Fluorescent Probe: Inhibition of Cell Division Protein FtsZ by mant-GTP Elucidated by NMR and Biochemical Approaches. ACS Chem. Biol. 2015, 10 (10), 2382-2392.

Sun, N. et al., Rational Design of Berberine-Based FtsZ inhibitors with Broad-Spectrum Antibacterial Activity. PLoS ONE 2014, 9 (5), e97514.

Domadia, P. N. et al., Berberine targets assembly of *Escherichia coli* cell division protein FtsZ. Biochemistry 2008, 47 (10), 3225-3234.

Artola, M. et al., Effective GTP-Replacing FtsZ Inhibitors and Antibacterial Mechanism of Action. ACS Chem. Biol. 2015, 10 (3), 834-843.

Ruiz-Avila, L. B. et al., Synthetic inhibitors of Bacterial Cell Division Targeting the GTP-Binding Site of FtsZ. ACS Chem. Biol. 2013, 8 (9), 2072-2083.

Chan, F. Y. et al., Identification of a New Class of FtsZ Inhibitors by Structure-Based Design and in Vitro Screening. Journal of Chemical Information and Modeling, 2013, 53 (8), 2131-2140.

Chan, F. Y. et al., Antimicrobial activity of a quinuclidine-based FtsZ inhibitor and its synergistic potential with beta-lactam antibiotics. Journal of antibiotics, 2015, 68 (4), 253-258.

Karpov, A. S. et al., Straightforward novel one-pot enaminone and pyrimidine syntheses by coupling-addition-cyclocondensation sequences. Synthesis 2003, (18), 2815-2826.

Clinical and Laboratory Standards Institute. Methods for Dilution Antimicrobial Susceptibility Tests for Bacteria That Grow Aerobically; Approved Standard, 7th ed.; CLSI document M07-A7; Clinical and Laboratory Standards Institute: Wayne, PA, 2006.

Tsai, C. J.-Y. et al., Galleria mellonella infection models for the study of bacterial diseases and for antimicrobial drug testing. Virulence 2016, 7, 214-229.

Mayer, M. et al., Characterization of Ligand Binding by Saturation Transfer Difference NMR Spectroscopy. Angew. Chem. Int. Ed. 1999, 38, 1784-1788.

Lam, T. et al., Structure-Based Design of New Dihydrofolate Reductase Antibacterial Agents: 7-(Benzimidazol-1-yl)-2,4-diaminoquinazolines. J. Med. Chem. 2014, 57, 651-668.

Anderson, D. E. et al., Comparison of Small Molecule Inhibitors of the Bacterial Cell Division Protein FtsZ and Identification of a Reliable Cross-Species Inhibitor. ACS Chem. Biol. 2012, 7, 1918-1928.

\* cited by examiner

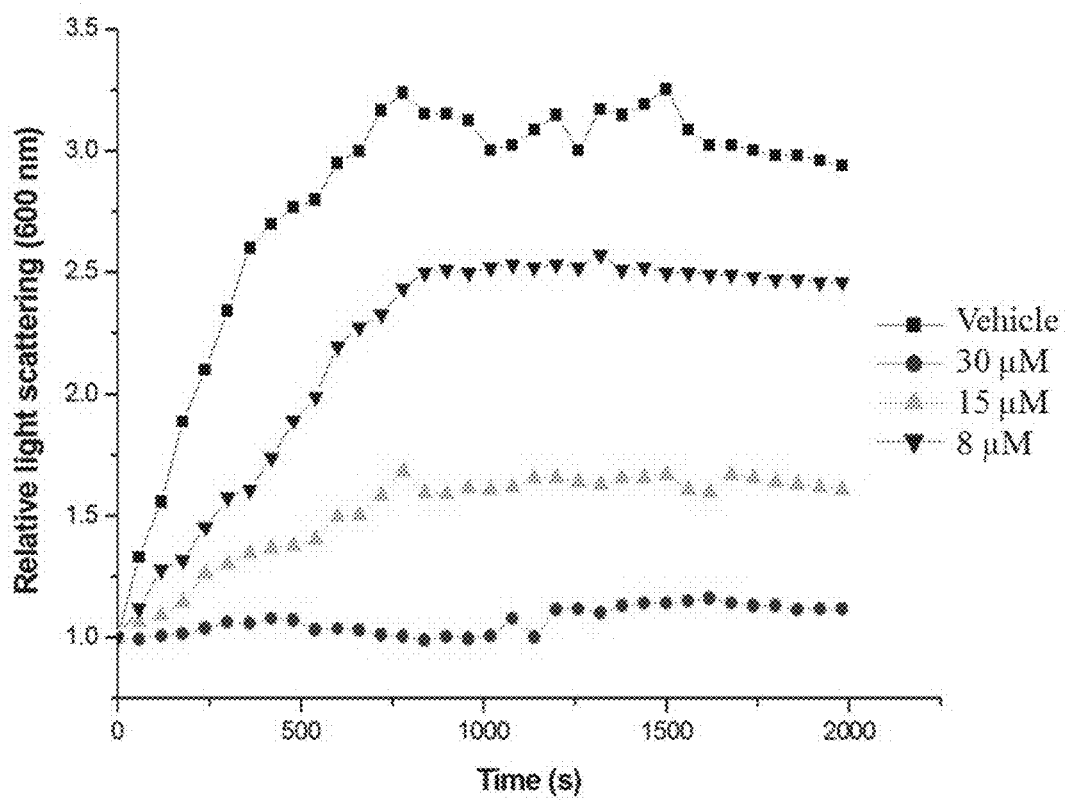

14dv_amine16

14dv_amine07

PYRIMIDINES FOR TREATMENT OF BACTERIAL INFECTIONS

CROSS-REFERENCE TO RELATED APPLICATIONS

This application claims the benefit of U.S. Provisional Application No. 62/319,894, filed Apr. 8, 2016. The entire contents and disclosures of the preceding application are incorporated by reference into this application.

Throughout this application, various publications are cited. The disclosures of these publications in their entireties are hereby incorporated by reference into this application to more fully describe the state of the art to which this invention pertains.

FIELD OF THE INVENTION

This invention relates to the synthesis of a novel series of amine linked 2,4,6-trisubstituted pyrimidines, which exhibited potent anti-staphylococcal activities by suppressing self-polymerization of cell division protein FtsZ.

BACKGROUND OF THE INVENTION

The inexorable rise in the incidence of serious bacterial infections caused by multiple antibiotic-resistant bacteria in healthcare and community associated settings has become a pressing threat of public health worldwide.[1] Of particular concern is the rise in incidence of methicillin resistant *Staphylococcus aureus* (MRSA) infections. MRSA is a human pathogen that can cause a wide range of illnesses, from mild skin and wound infections to pneumonia and bloodstream infections that cause sepsis and death. Centers for Disease Control and Prevention of United State estimates that over eighty thousand severe MRSA infections occur annually, resulting in eleven thousand deaths.[2] This scenario has driven the search for novel classes of anti-staphylococcal agents which act on novel bacterial drug targets.

The bacterial cell division machinery has been considered as an important field for exploring potential novel drug targets of antibacterial agents.[3] The filamenting temperature-sensitive mutant Z (FtsZ) protein undoubtedly represents one of the well-characterized and exploitable antibacterial drug targets.[4] FtsZ is a cytoplasmic protein and highly conserved tubulin-like guanosine triphosphatase (GTPase), playing an important role in bacterial cell division. In order for bacteria to carry out cell division, FtsZ monomers are required to localize mid-cell through the precise positioning of cell division site positioning protein and self-polymerize into single stranded straight protofilaments by means of head-to-tail association that curve upon hydrolysis of guanosine triphosphate (GTP) molecules.[5] Consecutive lateral contacts between FtsZ protofilaments produce FtsZ bundles, which eventually lead to formation of a contractile ring called Z-ring at the mid-cell. Following subsequent involvement of other downstream cell division proteins, Z-ring contraction and depolymerisation completes the cell division process to furnish identical daughter cells. Small molecules interfering initial stage of FtsZ polymerization are capable of blocking bacterial cell division, causing abrogation of bacterial cell viability eventually. These types of compounds have great potential to be developed as efficacious antimicrobial agents with a novel mode of action for clinical application. Several high resolution X-ray crystal structures of FtsZ homologs have been reported.[6] These results contributed to the knowledge regarding the general organization of FtsZ protein structure, which is known to comprise two independent folding domains (FIG. 1). The N-terminal domain forms a nucleotide binding site (GTP binding site, upper red circle of FIG. 1), while the C-terminal domain contains a flexible loop (T7 loop). Both domains were interconnected via a long central helix 7 (H7) of high rigidity.

Many FtsZ-interacting compounds have been discovered and reported to bind either the GTP binding site or a cleft formed by the H7 helix, T7 loop and C-terminal β sheet (FIG. 1, lower circle). Some exhibit potent antibacterial activity with minimum inhibitory concentration (MIC) at micromolar range. PC190723 (FIG. 2)[7] and its pro-drugs 1a[8] and 1b[9], and benzamide 2[10] have been demonstrated to exhibit in vitro and in vivo efficacy in a murine infection model. Moreover, X-ray crystallographic analysis revealed that PC190723 binds to a narrow cleft formed by the H7 helix, T7 loop and C-terminal β sheet (FIG. 1, lower circle).[11] However, analysis of PC190723 drug resistant mutants across various MRSA strains revealed that all PC190723 drug resistant isolates had multiple mutations, resulting in amino acid substitutions that mapped to the FtsZ protein.[12] These mutations mainly occurred at amino acid positions 193, 196 and 263 (FIG. 1), which accounted for over 90% of PC190723 drug resistant mutants. These results suggested that amino acid substitutions can alter slightly the overall shape of the binding pocket without interfering normal function of FtsZ. Nevertheless, this change resulted in PC190723 no longer binding to this pocket, therefore causing drug resistance. Such findings may hinder the potential of PC190723 and other related compounds[13] from being developed into agents that exhibit the potential to target the same binding pocket for further clinical development. On the other hand, several compounds targeting the GTP binding site of FtsZ have also been demonstrated to exhibit potent antibacterial activity, including natural product chrysophaentin A 3,[14] C8-substituted GTP analog 4[15], berberine analog 5[16] and naphthol derivative 6[17] (FIG. 2). Surprisingly, among these inhibitors, no drug resistant mutants have been reported in the literature so far presumably due to the fact that the GTP binding site is very important for recognizing the GTP molecule. Amino acid substitutions at this binding pocket may cause improper recognition of GTP molecule and thus hinder normal GTP hydrolysis process; therefore losing energy source to drive polymerization of FtsZ monomers.

Chan et al. identified a new class of FtsZ inhibitors exemplified by structure 7 bearing a 2,4,6-trisubstituted pyrimidine and a chiral aminoquinuclidine moiety (FIG. 2).[18] Molecular docking study of compound 7 and the GTP molecule using *S. aureus* FtsZ revealed that the 2,4,6-trisubstituted pyrimidine moiety of 7 occupied exactly the same binding pocket as the guanosine moiety of GTP molecule through an extensive network of hydrogen bonds with FtsZ protein, suggesting that the pyrimidine moiety is crucial for binding.[18] This class of compounds has been demonstrated to inhibit GTPase hydrolysis activity of *S. aureus* FtsZ at low micromolar $IC_{50}$ value with moderate antimicrobial activity against *S. aureus* and *E. coli*. Interestingly, compound 7a also exhibited strong synergistic effect against various MRSA and vancomycin-resistant *Enterococcus faecium* (VREF) strains when combined with clinically used β-lactam antibiotics.[19] However, structural complexity of the chiral quinuclidine scaffold and limited availability of compound have prevented further development. Accordingly, specially designed small molecules able to mimic and compete with GTP molecules to bind the GTP binding site of FtsZ may have greater potential to be developed as antimicrobial agents without acquiring drug resistance.

SUMMARY OF THE INVENTION

The present invention discloses an efficient synthesis of novel amine-linked 2,4,6-trisubstituted pyrimidine compounds with the aims of replacing the complex quinuclidine scaffold of 7 with simple amines and improving the antimicrobial activity and selectivity. Compounds exhibiting potent antimicrobial activity and low toxicity can be further investigated regarding its interaction with FtsZ protein. Because of their structural novelty, potent antimicrobial activity and high selectivity against *S. aureus*, a new series of such compounds may represent a promising therapy.

The present invention relates to a novel class of pyrimidine. A composition comprising the novel pyrimidine or its pharmaceutically acceptable salt, and a pharmaceutically acceptable carrier can be used to treat bacterial infection in a subject by administering to the subject an effective amount of the composition.

Definitions & Abbreviations

The following terms are used to describe the present invention. In the absence of a specific definition set forth herein, the terms used to describe the present invention shall be given their common meaning as understood by those of ordinary skill in the art.

As used herein, the expression "FtsZ" refers to Filamenting temperature-sensitive mutant Z.

As used herein, the term "GTP" refers to guanosine triphosphate.

As used herein, the term "GTPase" refers to guanosine triphosphatase.

As used herein, the term "MIC" refers to minimum inhibition concentration.

As used herein, the term "MRSA" refers to methicillin resistant *Staphylococcus aureus*.

As used herein, the term "VREF" refers to vancomycin-resistant *Enterococcus faecium*.

As used herein, the term "ACN" refers to acetonitrile.

As used herein, the term "Boc" refers to tert-butyloxycarbonyl.

As used herein, the term "ACN" refers to acetonitrile.

As used herein, the term "CBr$_4$" refers to carbon tetrabromide.

As used herein, the term "CuI" refers to copper (I) iodide.

As used herein, the term "DCM" refers to dichloromethane.

As used herein, the term "DMSO" refers to dimethyl sulfoxide.

As used herein, the term "EA" refers to ethyl acetate.

As used herein, the term "EDTA" refers to ethylenediaminetetraacetic acid.

As used herein, the term "HCl" refers to hydrochloric acid.

As used herein, the term "Hex" refers to hexane.

As used herein, the term "MeOH" refers to methanol.

As used herein, the term "MgSO$_4$" refers to magnesium sulphate.

As used herein, the term "Na$_2$CO$_3$" refers to sodium carbonate.

As used herein, the term "NaCl" refers to sodium chloride.

As used herein, the term "NaOH" refers to sodium hydroxide.

As used herein, the term "NEt$_3$" refers to triethylamine.

As used herein, the term "NH$_4$HCO$_3$" refers to ammonium bicarbonate.

As used herein, the term "Pd(PPh$_3$)$_2$Cl$_2$" refers to bis(triphenylphosphine)palladium(II) dichloride.

As used herein, the term "PMSF" refers to phenylmethylsulfonyl fluoride.

As used herein, the term "PPh$_3$" refers to triphenylphosphine.

As used herein, the term "TFA" refers to trifluoroacetic acid.

As used herein, the term "THF" refers to tetrahydrofuran.

As used herein, the term "Tris-HCl" refers to tris(hydroxymethyl)aminomethane hydrochloride.

As used herein, the term "NMR" refers to nuclear magnetic resonance.

As used herein, the term "CDCl$_3$" refers to deuterated chloroform.

As used herein, the term "ESI" refers to electron spray ionization.

As used herein, the term "TLC" refers to thin-layer chromatography.

As used herein, the term "aryl" refers to a phenyl or naphthyl group optionally substituted with an appropriate substituent.

As used herein, the term "heteroaryl" refers to a six-membered aromatic ring or two fused 6-membered aromatic rings containing at least one nitrogen (N) as the heteroatom, and optionally substituted with an appropriate substituent.

As used herein, the term "optionally substituted phenyl" means that the phenyl group is unsubstituted or substituted with, but not limited to, halogen (F, Cl, Br), methyl, trifluoromethyl, methoxy, pyridyl, butyl, ethyl and propyl.

As used herein, the term "optionally substituted benzyl" means that the aromatic ring of the benzyl group is unsubstituted or substituted with, but not limited to, halogen (F, Cl, Br), methyl, trifluoromethyl, methoxy, pyridyl, butyl, ethyl and propyl.

As used herein, the term "optionally substituted benzoyl" means that the aromatic ring of the benzoyl group is unsubstituted or substituted with, but not limited to, halogen (F, Cl, Br), methyl, trifluoromethyl, methoxy, pyridyl, butyl, ethyl and propyl.

As used herein, the term "optionally substituted phenethyl" means that the aromatic ring of the phenethyl group is unsubstituted or substituted with, but not limited to, halogen (F, Cl, Br), methyl, trifluoromethyl, methoxy, pyridyl, butyl, ethyl and propyl.

As used herein, the term "optionally substituted cinnamoyl" means that the aromatic ring of the cinnamoyl group is unsubstituted or substituted with, but not limited to, halogen (F, Cl, Br), methyl, trifluoromethyl, methoxy, pyridyl, butyl, ethyl and propyl.

conc. HCl, MeOH, r.t. 2 h; Step (c): PPh$_3$, CBr$_4$, THF, r.t. 3-4 h; Step (d): amine01-39 (please refer to Table 2 for chemical structures), ACN, r.t. 24 h.

Figure 4:
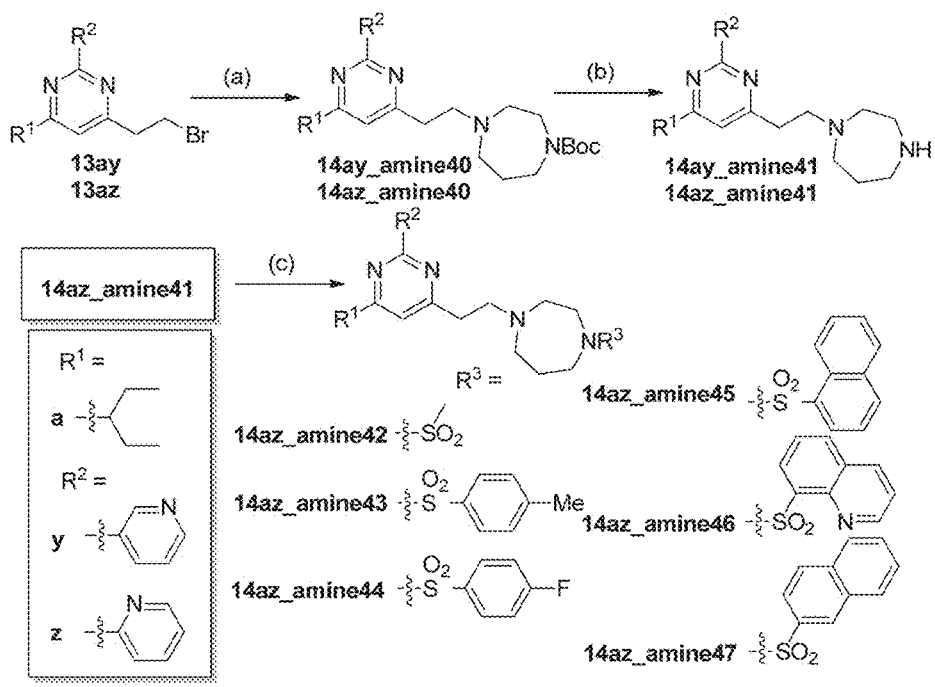

FIG. 4 shows the synthesis of pyrimidines with a sulfonamide group. Step (a): 1-Boc-homopiperazine, ACN, rt., 14 h; Step (b): TFA, DCM, 0° C., 2 h; Step (c): various sulfonyl chloride, NEt$_3$, DCM, 0° C., 3 h.

Figure 5:
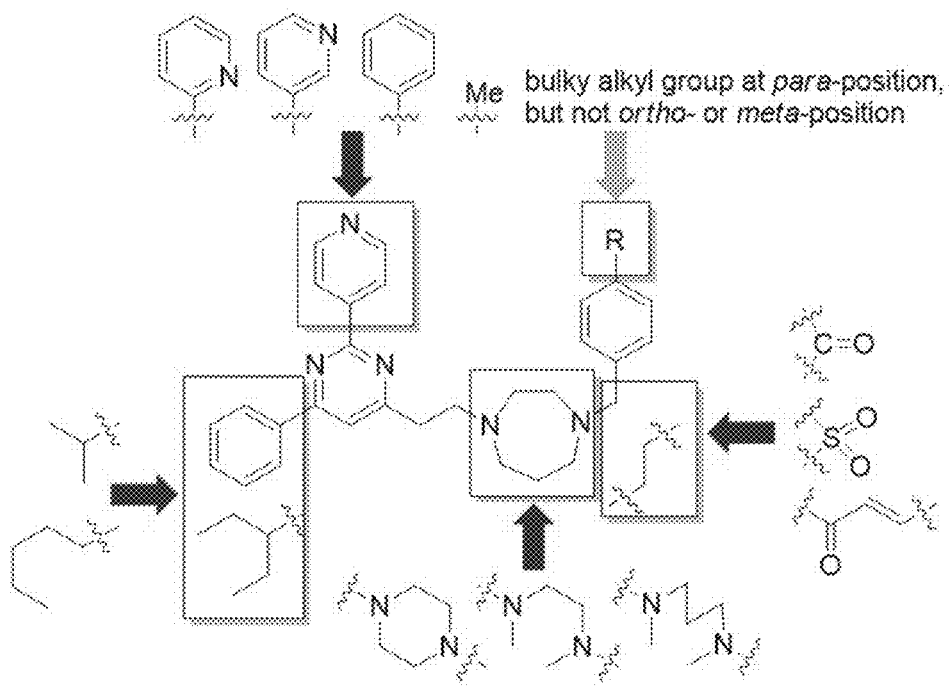

FIG. 5 shows a summary of SAR study. Black arrow indicates unfavorable substituents and grey arrow indicates favorable substituents.

Figure 6:
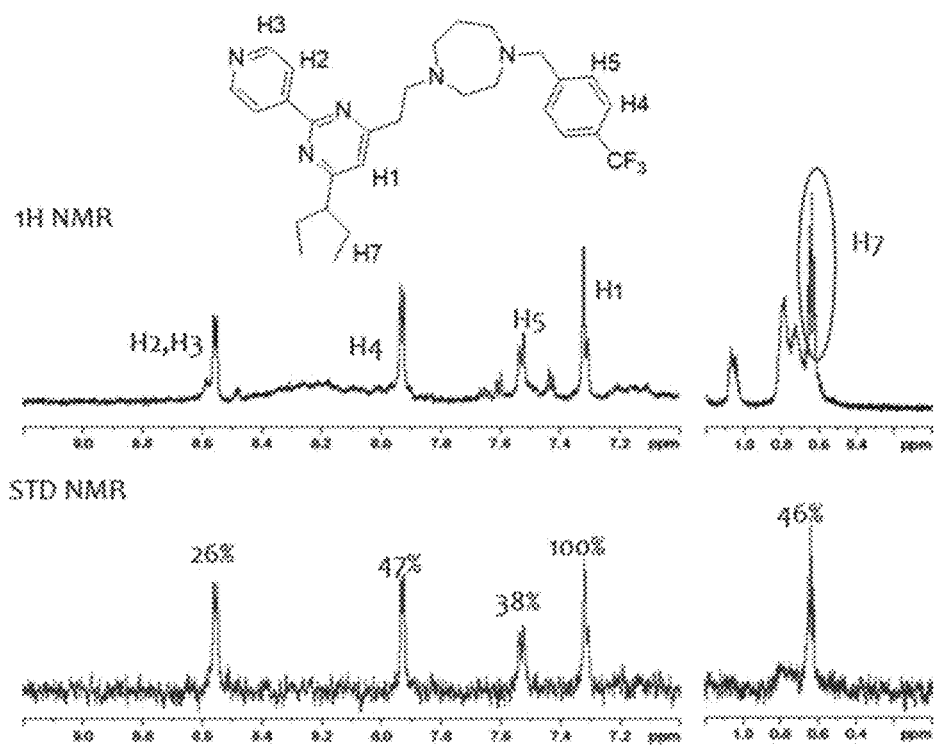

FIG. 6 shows a 1D (STD-off) spectrum of compound 14av_amine16 binding to the *S. aureus* FtsZ protein, with signal assignment (upper panel); and a corresponding Saturation Transfer Difference (STD) spectrum (lower panel) showing the STD effect ($I_{STD}/I_0$) for each proton.

FIG. 7 shows the effect of compound 14av_amine16 on polymerization of the *S. aureus* FtsZ protein at various concentrations.

Figure 8A:
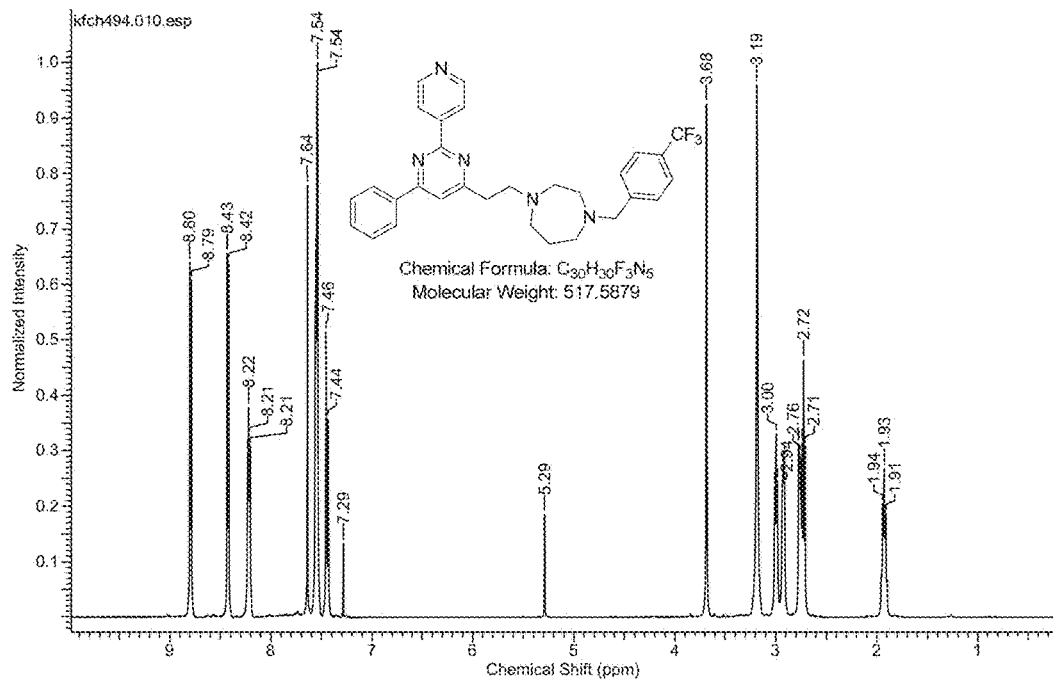
Figure 8B:
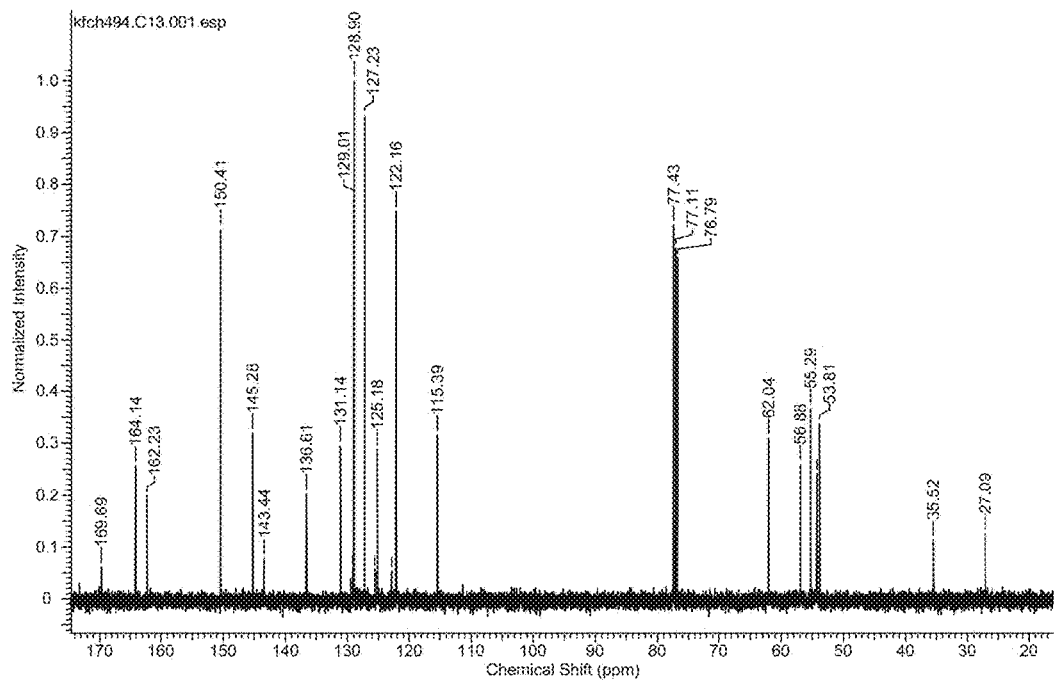
Figures 9A, 9B:
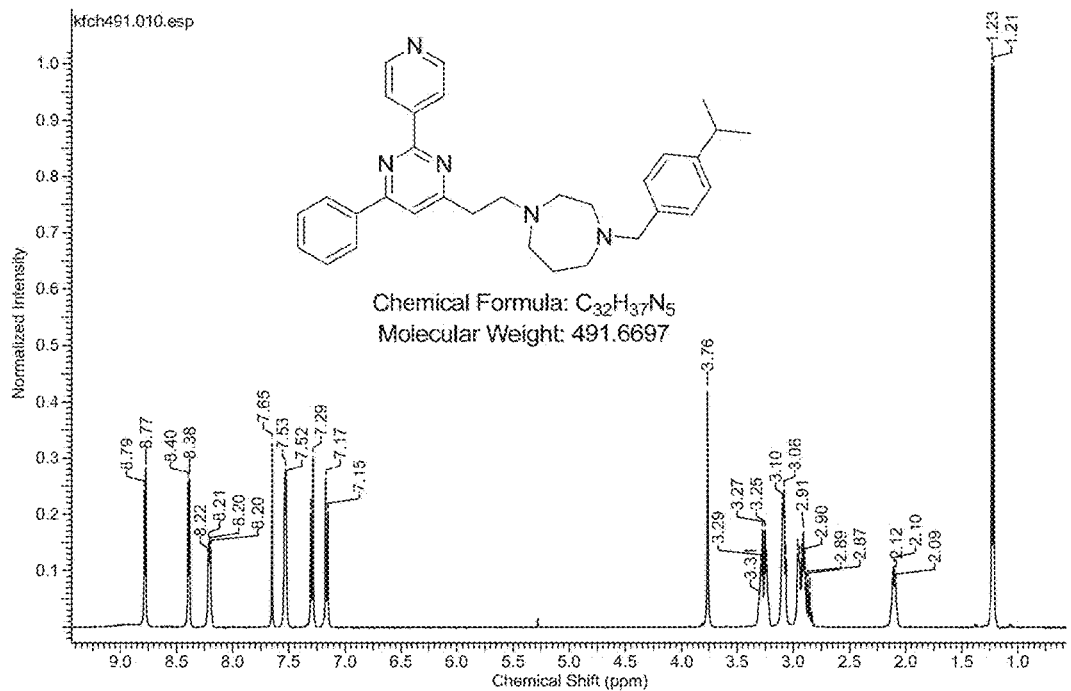
Figure 10A:
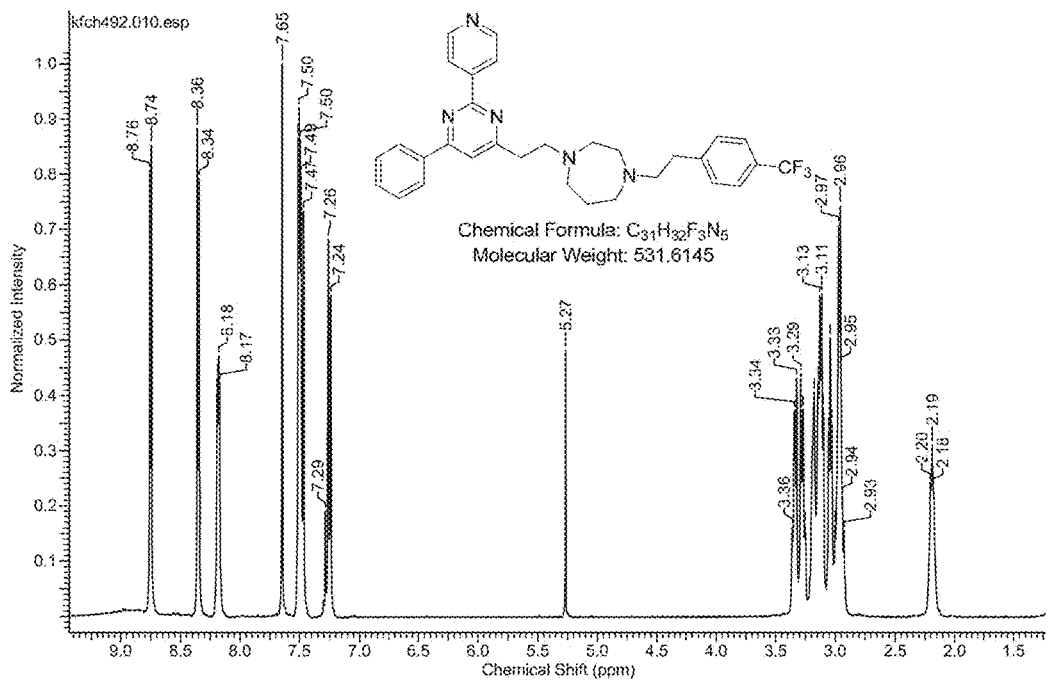
Figure 10B:
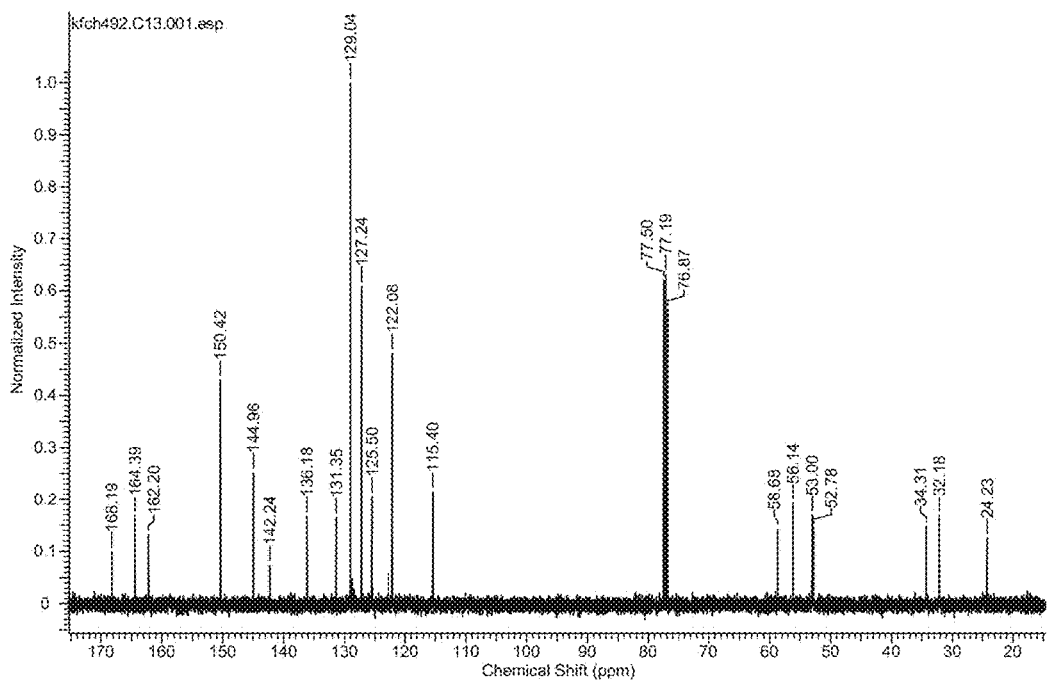
Figure 11A:
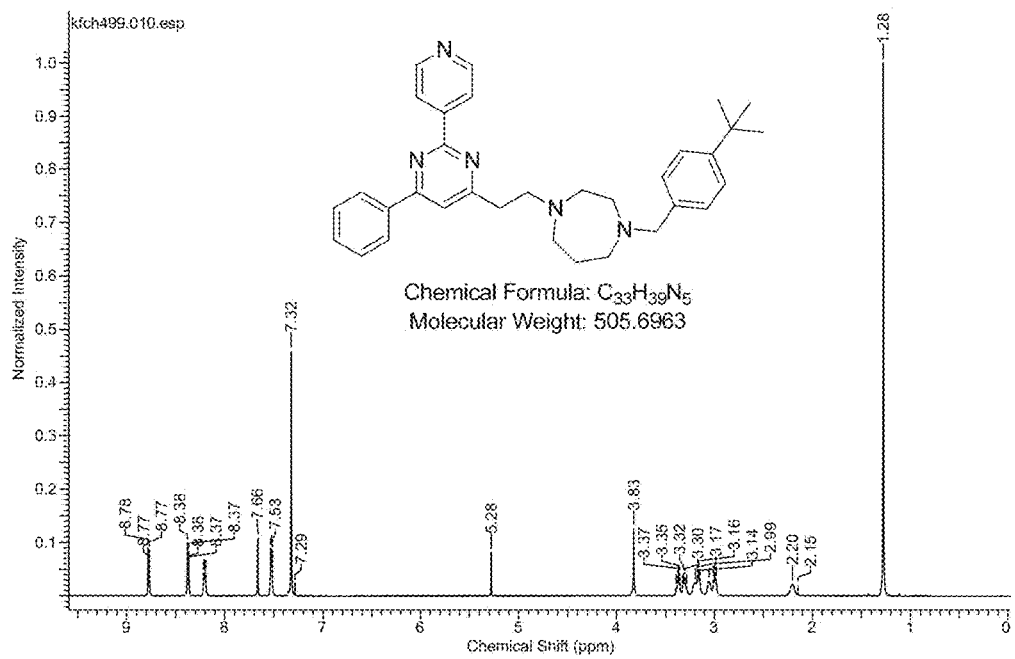
Figure 11B:
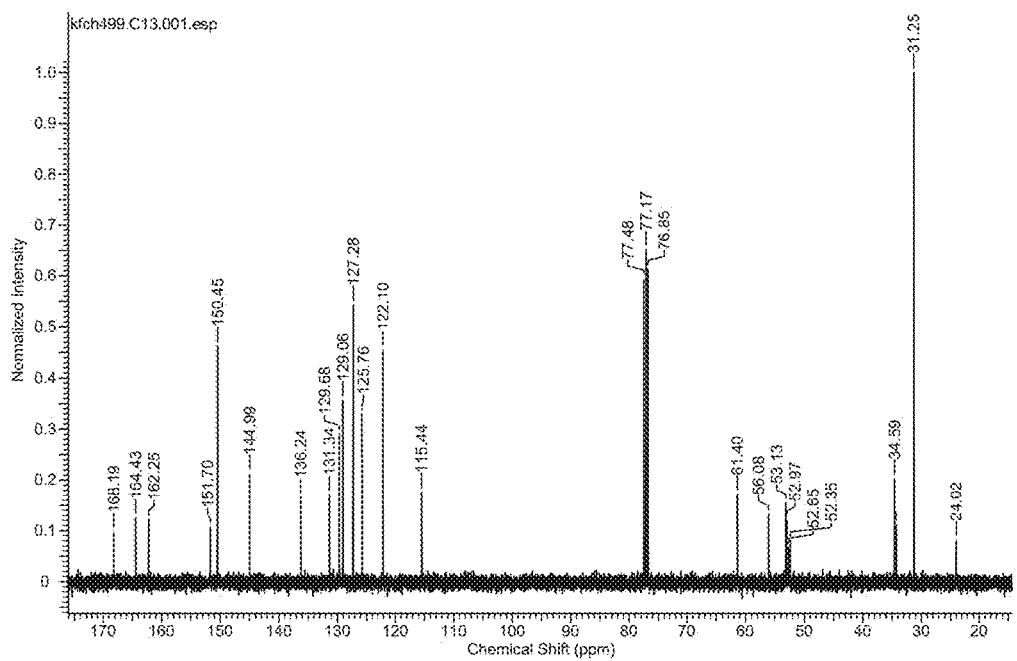
Figure 12A:
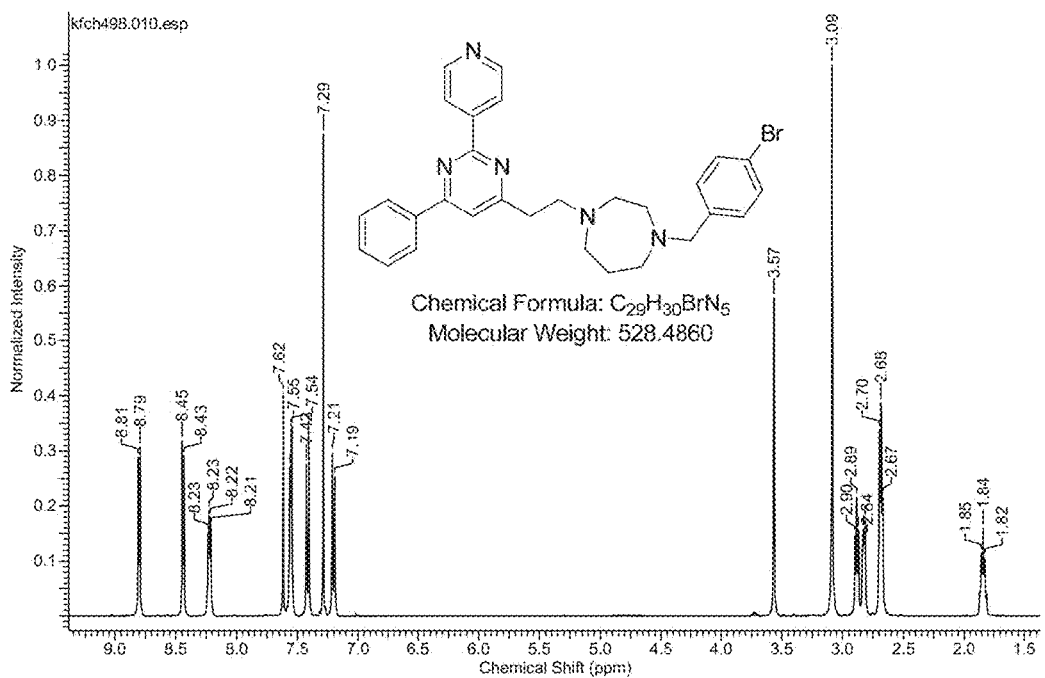
Figure 12B:
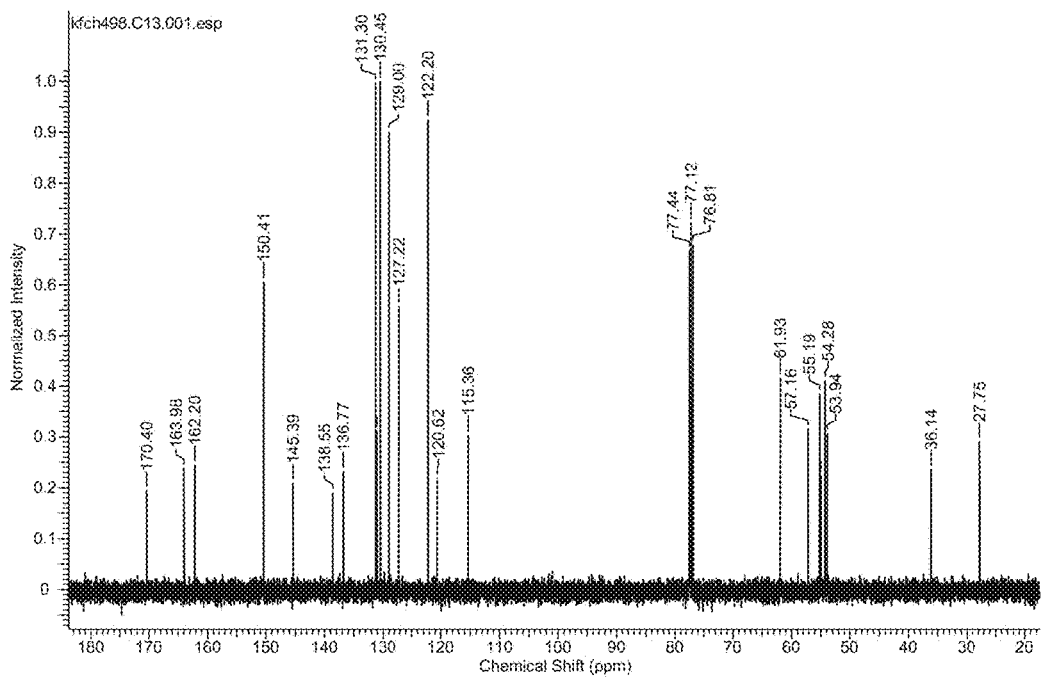
Figure 13A:
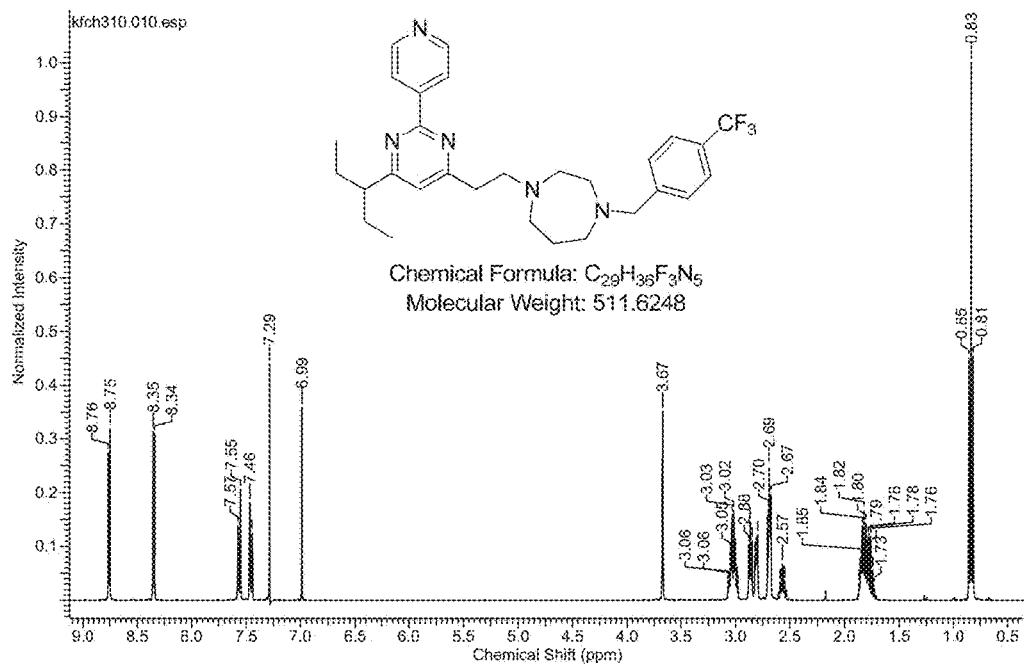
Figure 13B:
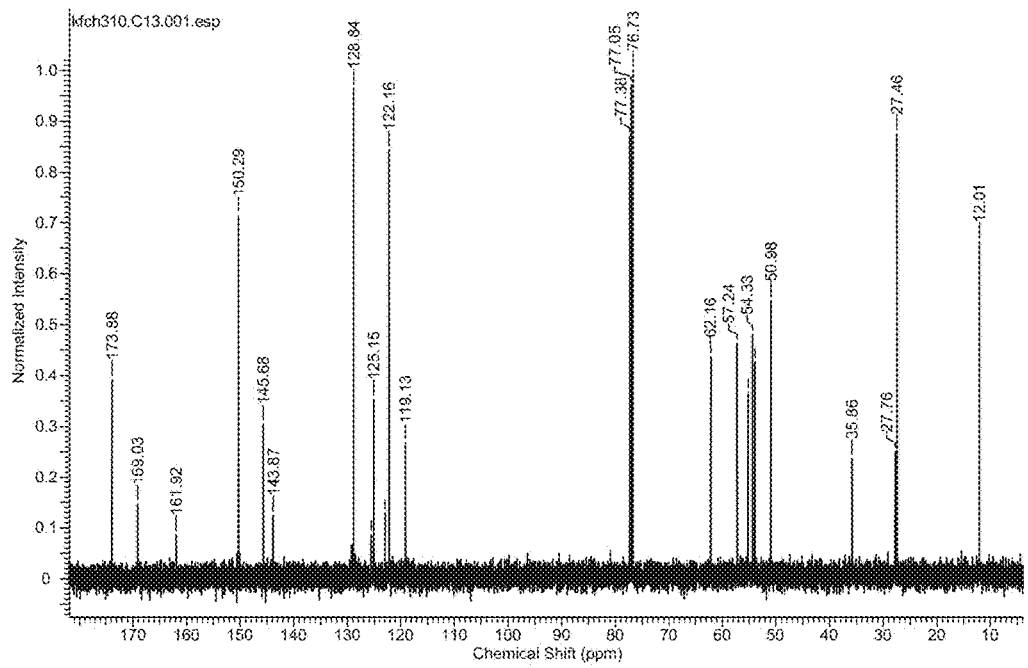
Figure 14A:
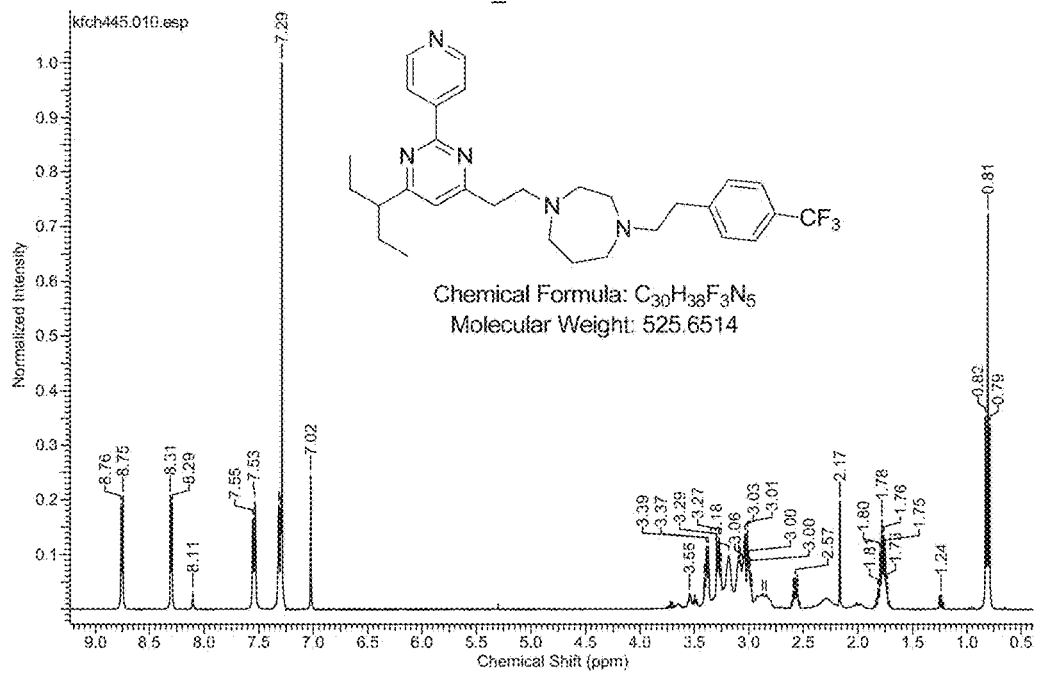
Figure 14B:
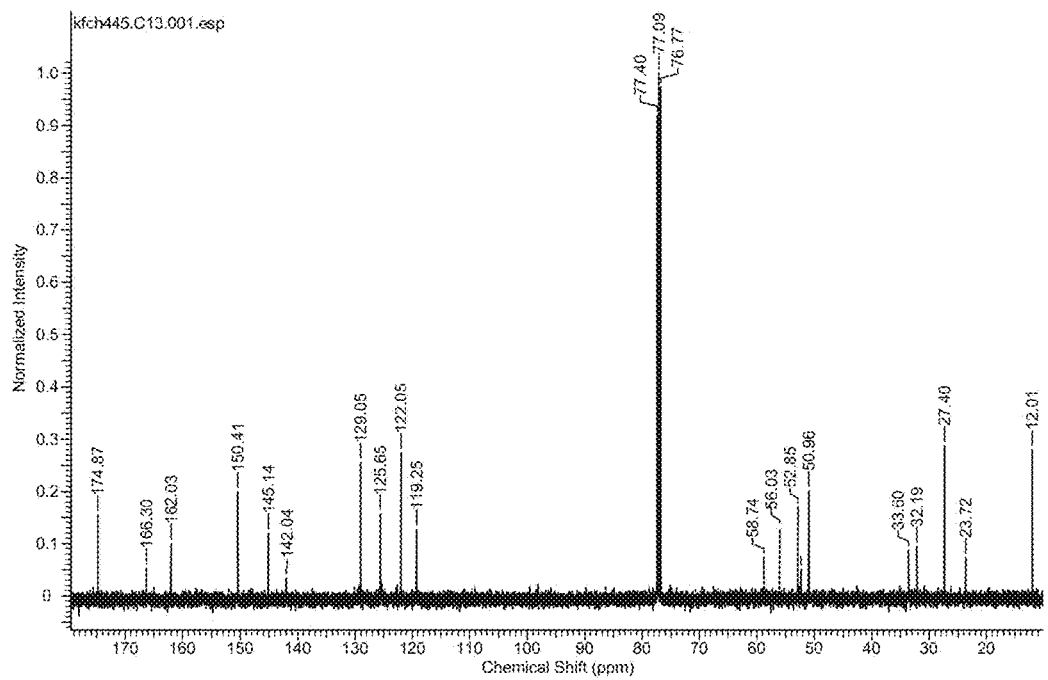
Figure 15A:
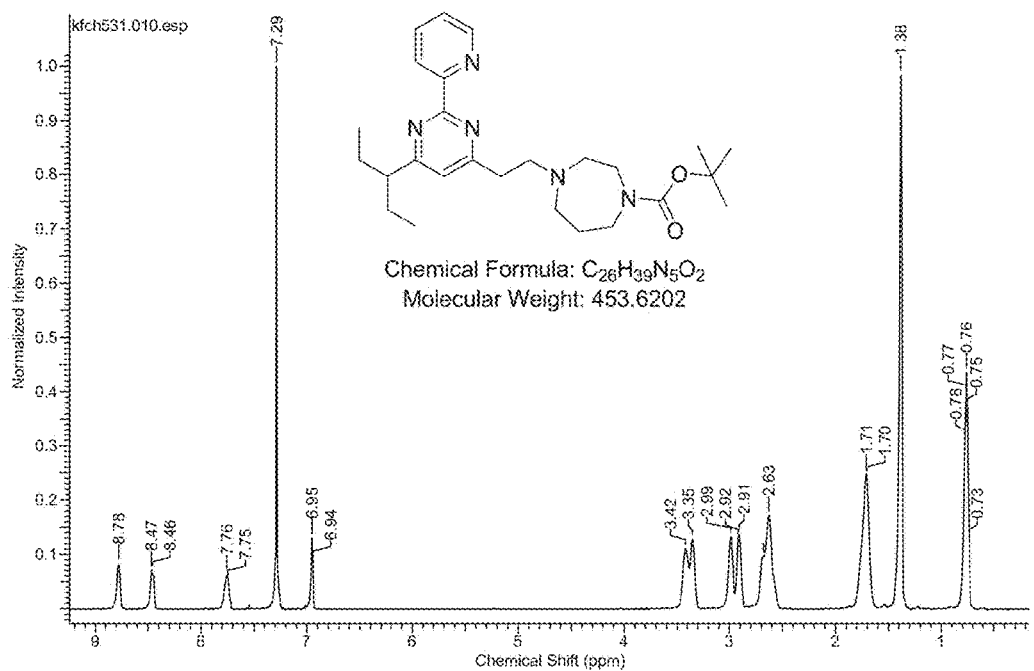
Figure 15B:
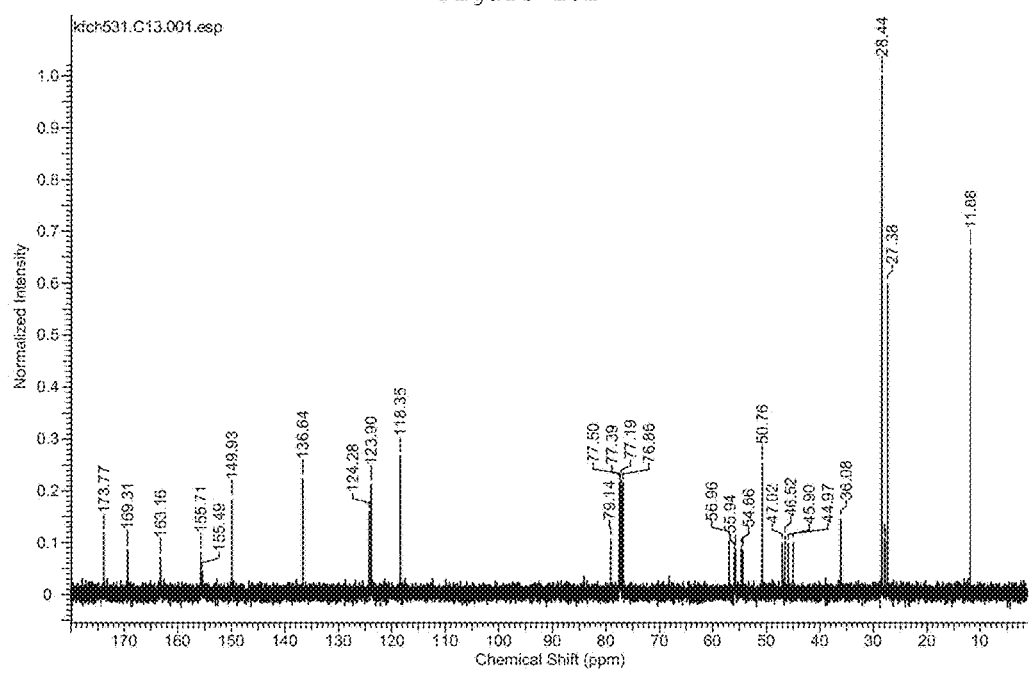
Figure 16A:
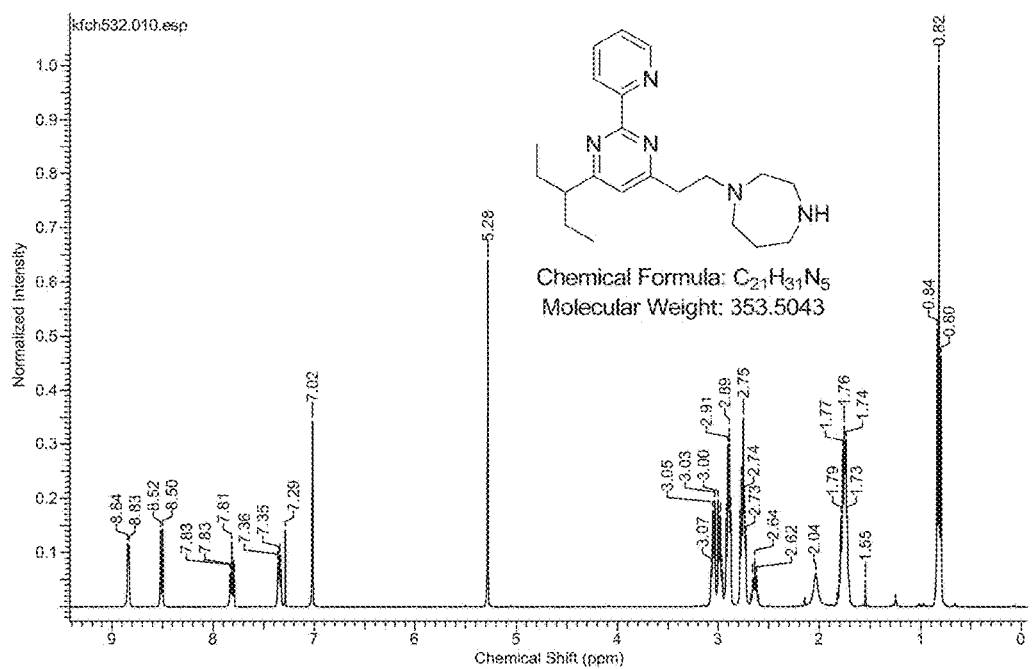
Figure 16B:
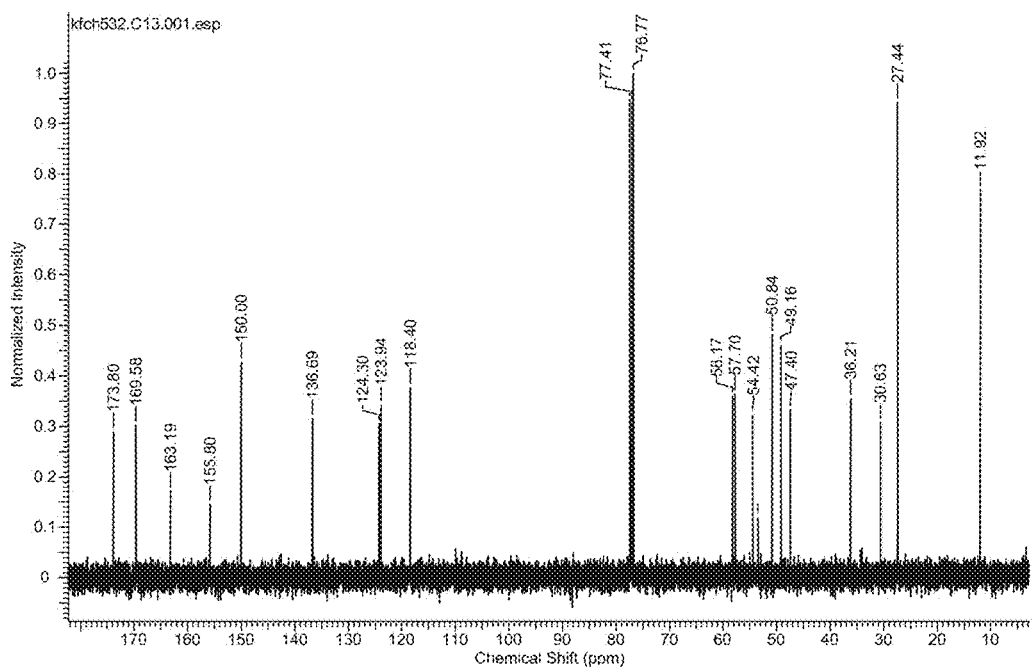
Figure 17A:
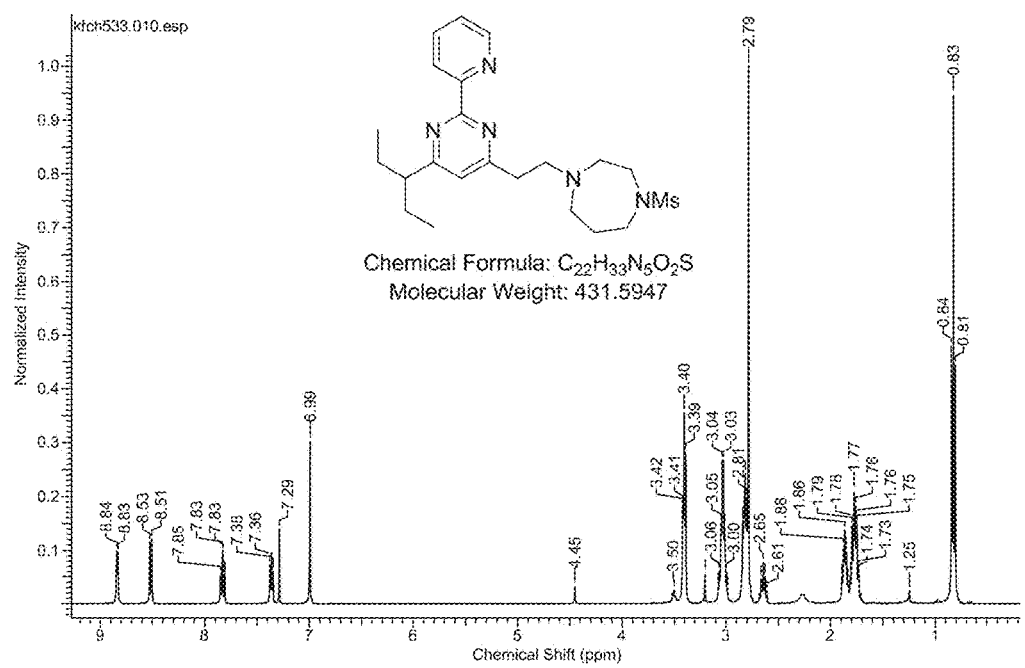
Figure 17B:
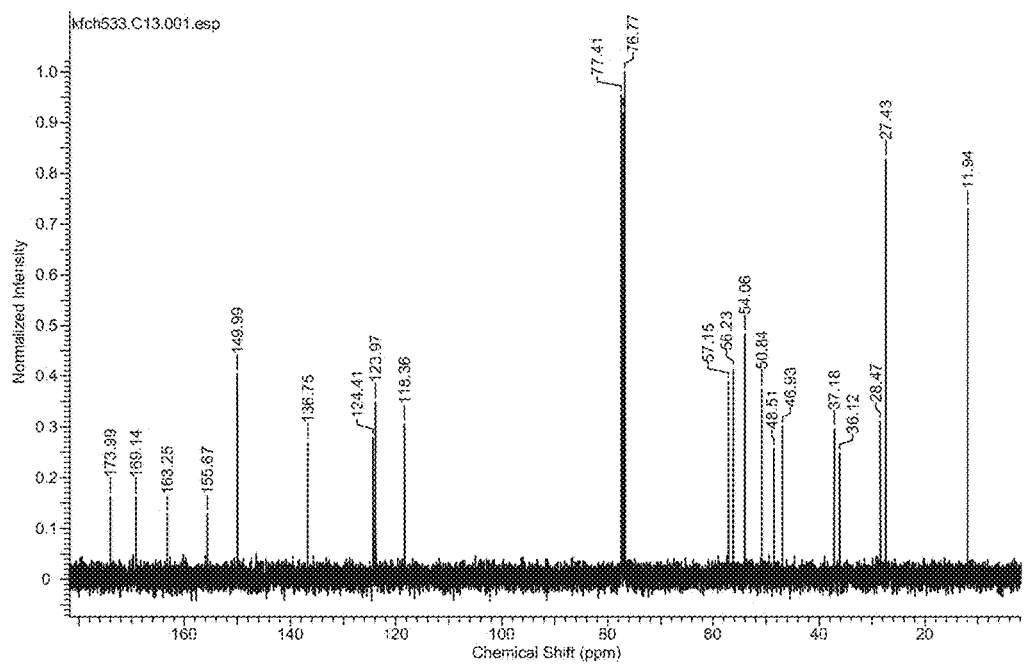

FIG. 8A is $^1$H NMR of 14dv_amine16
FIG. 8B is $^{13}$C NMR of 14dv_amine16.
FIG. 9A is $^1$H NMR of 14dv_amine06.
FIG. 9B is $^{13}$C NMR of 14dv_amine06.
FIG. 10A is $^1$H NMR of 14dv_amine20.
FIG. 10B is $^{13}$C NMR of 14dv_amine20.
FIG. 11A is $^1$H NMR of 14dv_amine07.
FIG. 11B is $^{13}$C NMR of 14dv_amine07.
FIG. 12A is $^1$H NMR of 14dv_amine08.
FIG. 12B is $^{13}$C NMR of 14dv_amine08.
FIG. 13A is $^1$H NMR of 14av_amine16.
FIG. 13B is $^{13}$C NMR of 14av_amine16.
FIG. 14A is $^1$H NMR of 14av_amine20.
FIG. 14B is $^{13}$C NMR of 14av_amine20.
FIG. 15A is $^1$H NMR of 14az_amine40.
FIG. 15B is $^{13}$C NMR of 14az_amine40.
FIG. 16A is $^1$H NMR of 14az_amine41.
FIG. 16B is $^{13}$C NMR of 14az_amine41.
FIG. 17A is $^1$H NMR of 14az_amine42.
FIG. 17B is $^{13}$C NMR of 14az_amine42.

Figure 18A:
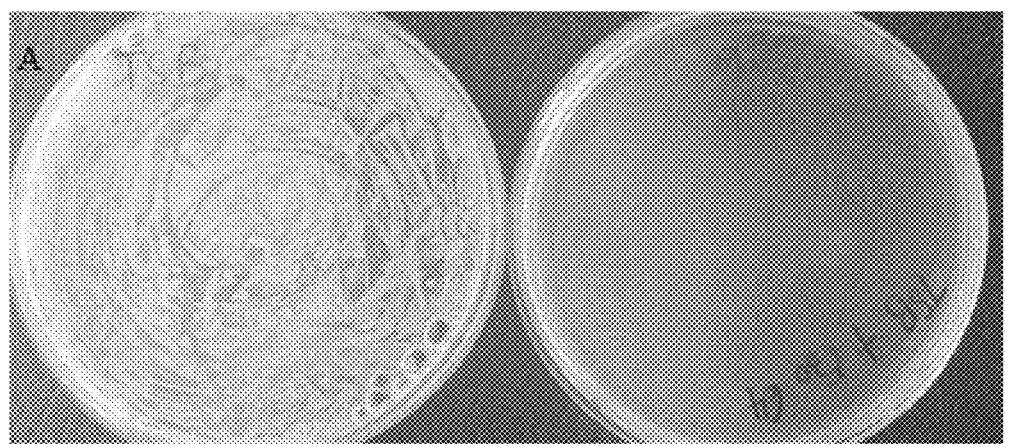

FIG. 18A shows the frequency of resistance (FOR) study of bacterial growth in agar plates after treatment with DMSO (left) and 14av_amine16 (right).

Figure 18B:
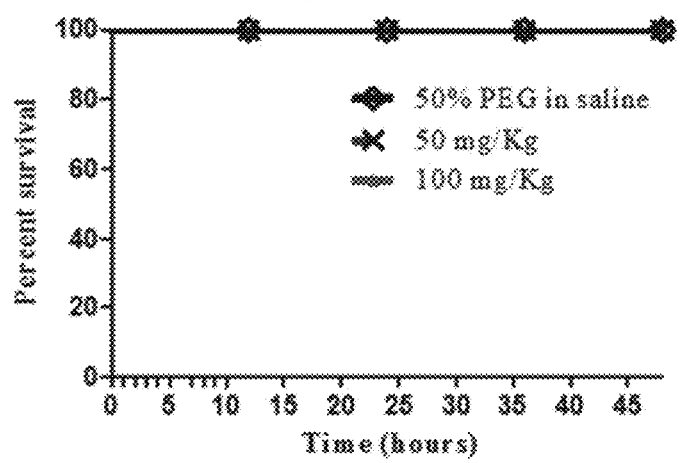
Figure 18C:
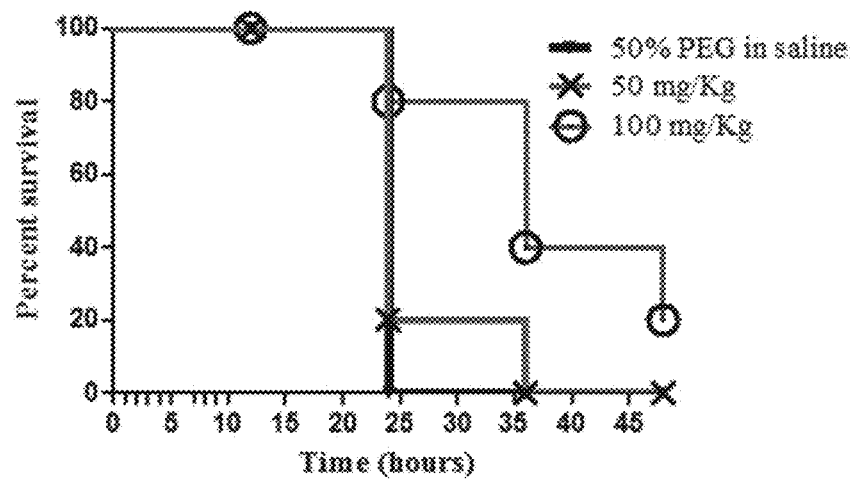

FIG. 18B shows the Kaplan-Meier survival analysis of *G. mellonella* larvae following injection of various concentrations of compound 14av_amine16 without lethal dose of MRSA ATCC 43300 inoculation. FIG. 18C Kaplan-Meier survival analysis of *G. mellonella* larvae following injection of various concentrations of compound 14av_amine16 with lethal dose of MRSA ATCC 43300 inoculation. Larvae were considered dead if they did not respond to physical stimuli. Data presented are the mean of three independent assays.

Figure 19A:
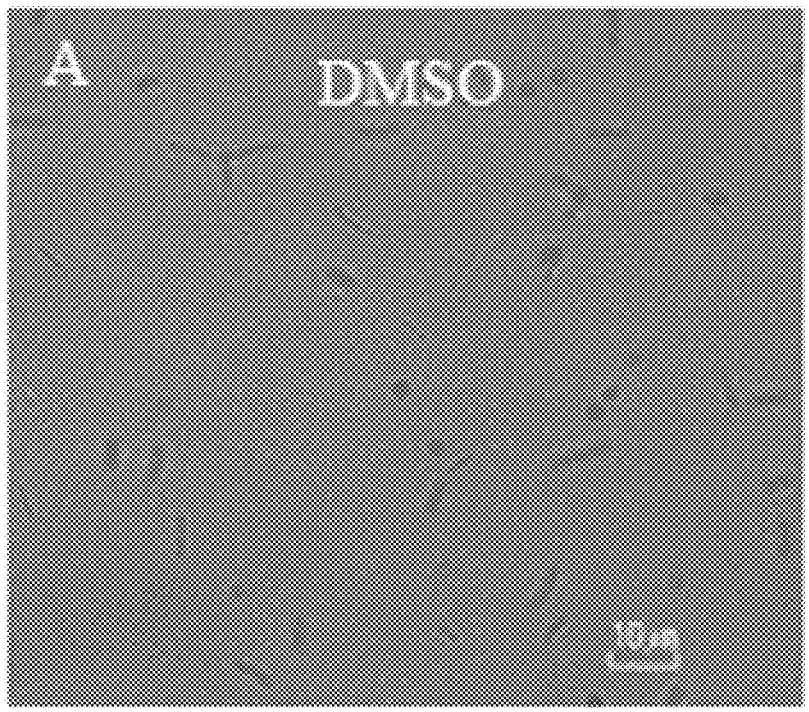
Figure 19B:
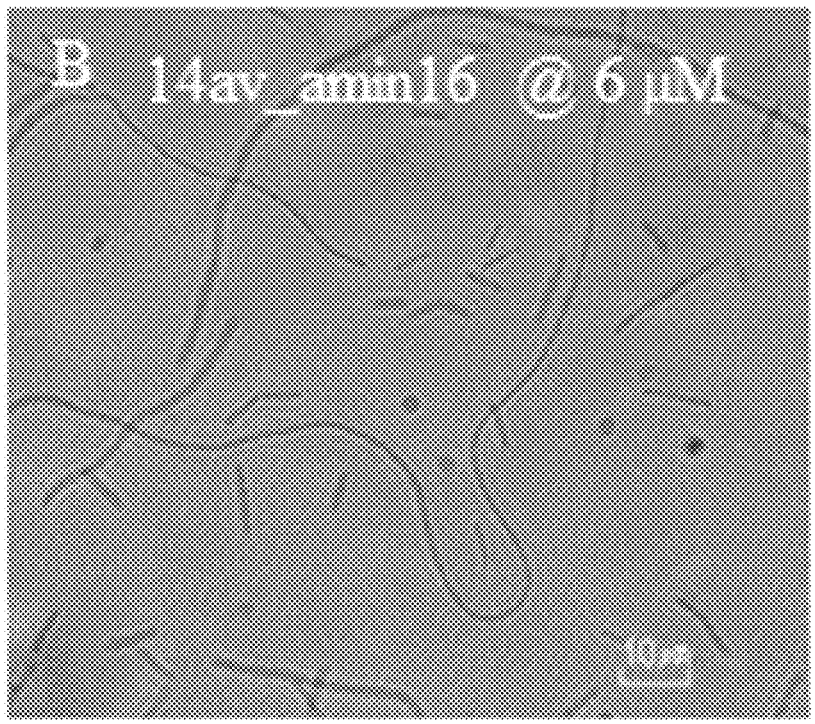
Figure 19C:
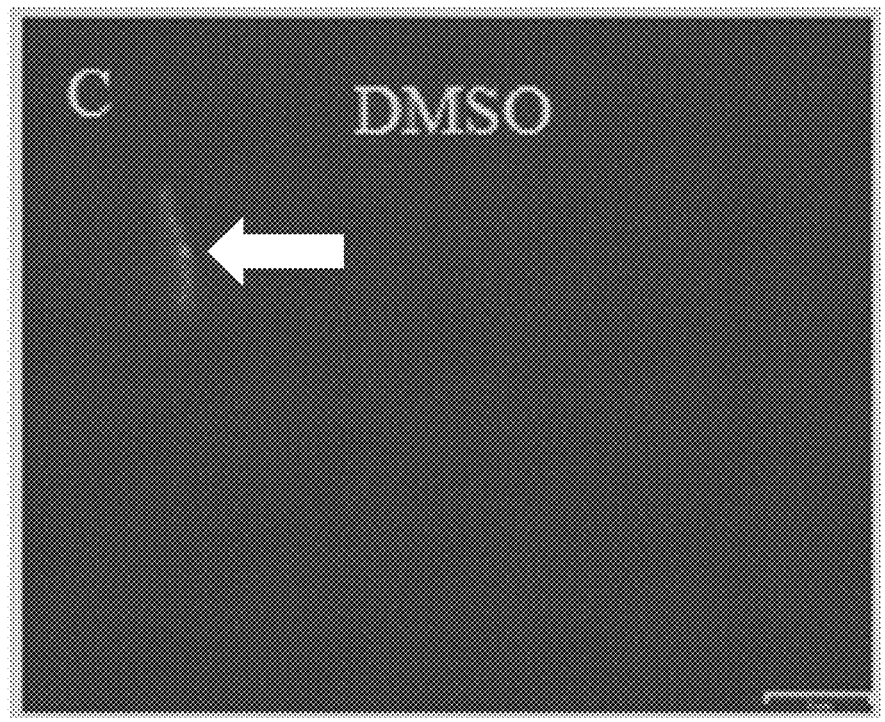
Figure 19D:
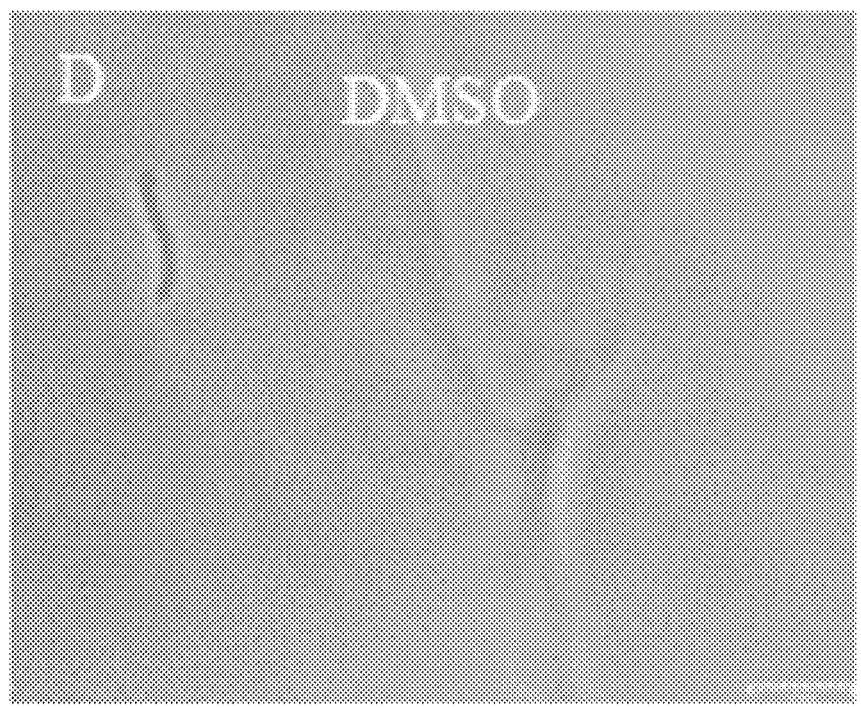
Figure 19E:
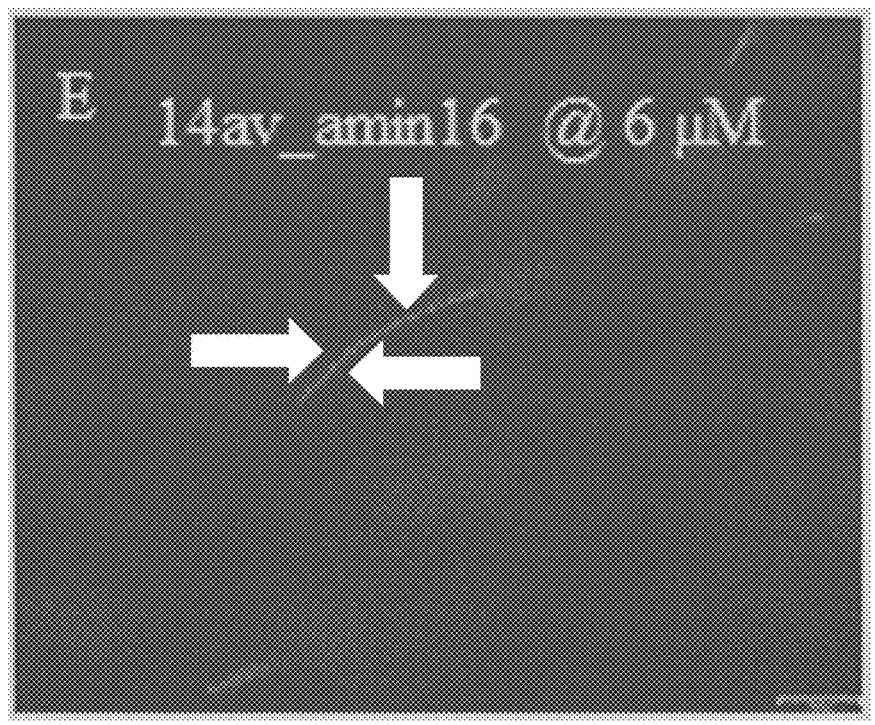
Figure 19F:
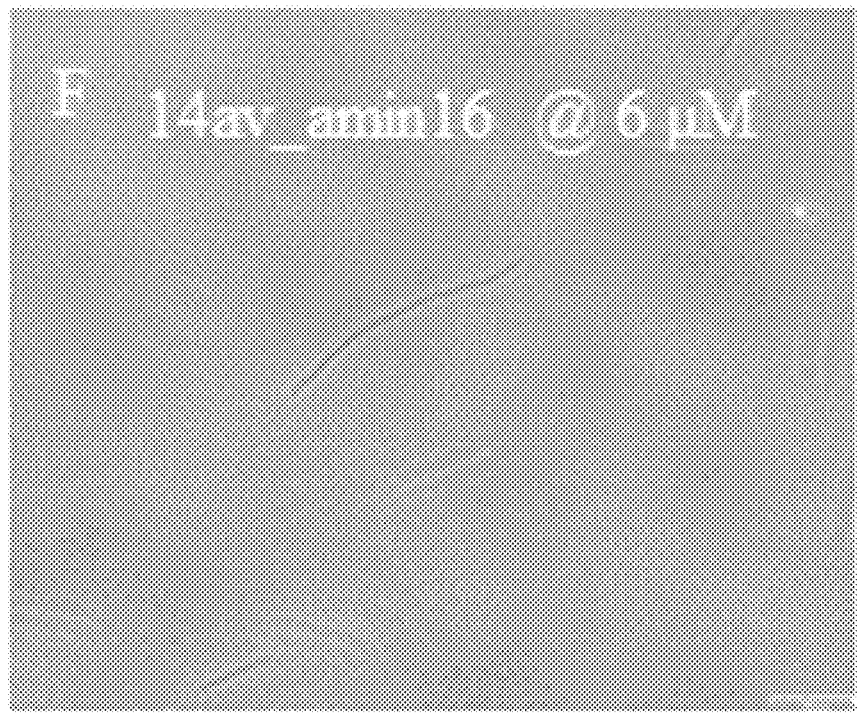

FIGS. 19A-19F are the microscopic observation of a rod-shaped *B. subtilis* 168 cell morphology after treatment with DMSO or compound 14av_amine16. FIG. 19A shows the effect of DMSO treatment on the cell morphology of *B. subtilis* 168. FIG. 19B shows the effect of compound 14av_amine16 treatment on the cell morphology of *B. subtilis* 168. FIG. 19C shows the DMSO treated *B. subtilis* 168 with a functional green fluorescent protein tagged FtsZ. FIG. 19D shows the corresponding phase-contrast microscopic pictures of FIG. 19C. FIG. 19E shows compound 14av_amine16 treated *B. subtilis* 168 with a functional green fluorescent protein tagged FtsZ. FIG. 19F shows the corresponding phase-contrast microscopic pictures of FIG. 19E.

DETAILED DESCRIPTION OF THE INVENTION

Figure 2:
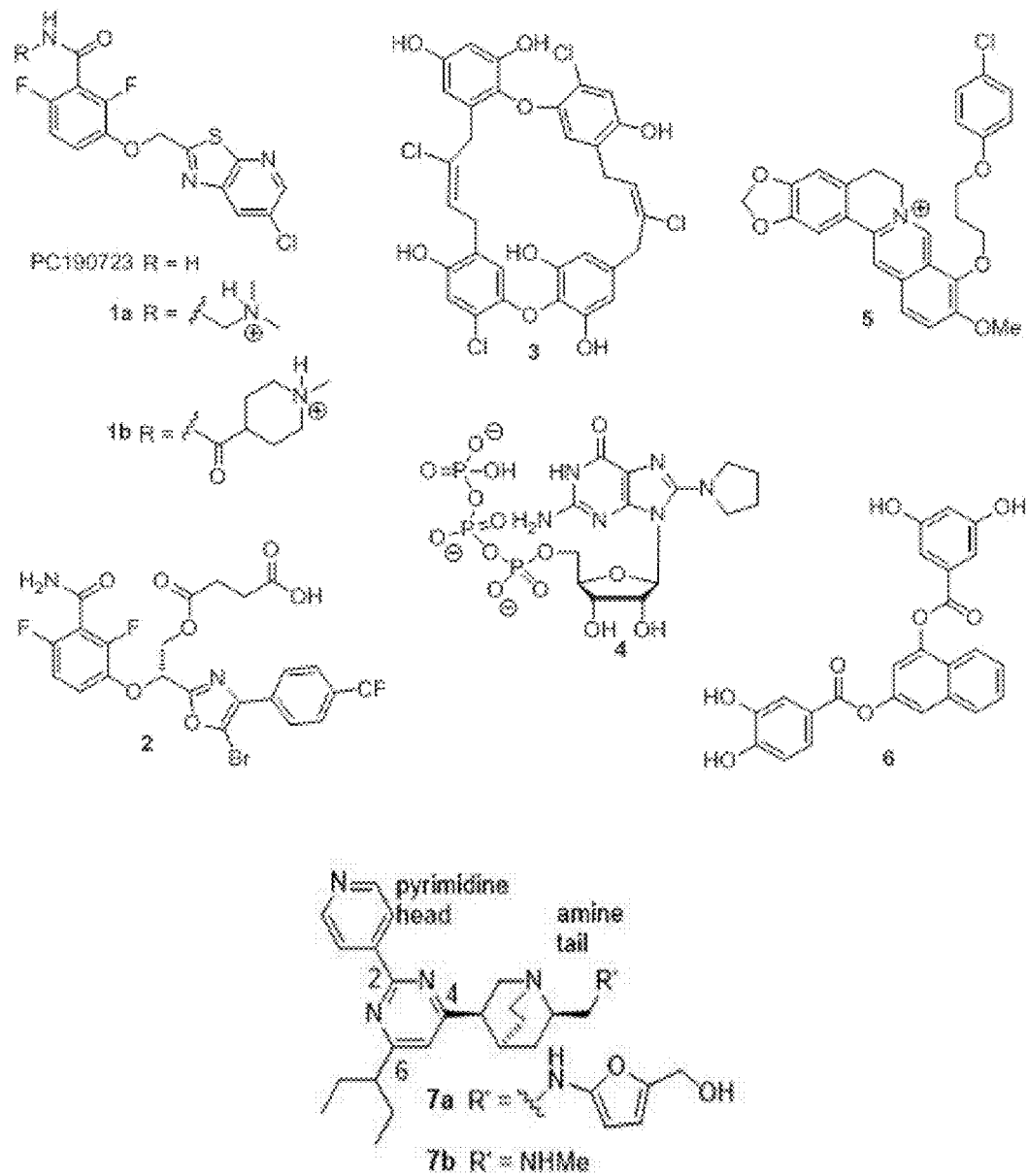
FIG. 2 shows the chemical structures of FtsZ inhibitors 1-7.

The present invention discloses an efficient synthesis of a novel amine-linked 2,4,6-trisubstituted pyrimidine compound library with the aims of replacing the complex quinuclidine scaffold of 7 and improving the antimicrobial activity and selectivity. Compound 7 was divided into two parts (pyrimidine head and amine tail) as outlined in FIG. 2. Based on this approach, different pyrimidine heads and amine tails were used to assemble compound 14 of the present invention. Some examples of 14 were illustrated by Tables 1 and 2, but were not meant to limit the scope of the invention. The amine tails include homopiperazine (amine01-23), piperazine (amine24-34) and linear amines (amine 35-39).

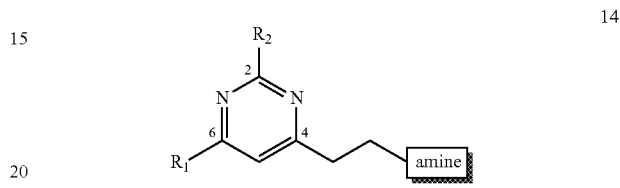

TABLE 1

| Examples of 2,4,6-trisubstituted pyrimidine 14 | |
|---|---|
| Entry | 2,4,6-trisubstituted pyrimidine |
| 1 | 14av_amine01 |
| 2 | 14av_amine02 |
| 3 | 14av_amine03 |
| 4 | 14av_amine04 |
| 5 | 14av_amine05 |
| 6 | 14av_amine06 |
| 7 | 14av_amine07 |
| 8 | 14av_amine08 |
| 9 | 14av_amine09 |
| 10 | 14av_amine10 |
| 11 | 14av_amine11 |
| 12 | 14av_amine12 |
| 13 | 14av_amine13 |
| 14 | 14av_amine14 |
| 15 | 14av_amine15 |
| 16 | 14av_amine16 |
| 17 | 14av_amine17 |
| 18 | 14av_amine18 |
| 19 | 14av_amine19 |
| 20 | 14av_amine20 |
| 21 | 14av_amine21 |
| 22 | 14av_amine22 |
| 23 | 14av_amine23 |
| 24 | 14av_amine24 |
| 25 | 14av_amine25 |
| 26 | 14av_amine26 |
| 27 | 14av_amine27 |
| 28 | 14av_amine28 |
| 29 | 14av_amine29 |
| 30 | 14av_amine30 |
| 31 | 14av_amine31 |
| 32 | 14av_amine32 |
| 33 | 14av_amine33 |
| 34 | 14av_amine34 |
| 35 | 14av_amine35 |
| 36 | 14av_amine36 |
| 37 | 14av_amine37 |
| 38 | 14av_amine38 |
| 39 | 14av_amine39 |
| 40 | 14aw_amine06 |
| 41 | 14aw_amine07 |
| 42 | 14aw_amine16 |
| 43 | 14ax_amine06 |
| 44 | 14ax_amine07 |
| 45 | 14ax_amine16 |
| 46 | 14ay_amine04 |
| 47 | 14ay_amine05 |

TABLE 1-continued

Examples of 2,4,6-trisubstituted pyrimidine 14

| Entry | 2,4,6-trisubstituted pyrimidine |
|---|---|
| 48 | 14ay_amine08 |
| 49 | 14ay_amine09 |
| 50 | 14ay_amine12 |
| 51 | 14ay_amine13 |
| 52 | 14ay_amine16 |
| 53 | 14ay_amine17 |
| 54 | 14ay_amine18 |
| 55 | 14ay_amine20 |
| 56 | 14az_amine07 |
| 57 | 14az_amine08 |
| 58 | 14az_amine09 |
| 59 | 14az_amine12 |
| 60 | 14az_amine16 |
| 61 | 14az_amine17 |
| 62 | 14az_amine18 |
| 63 | 14az_amine20 |
| 64 | 14bv_amine02 |
| 65 | 14bv_amine04 |
| 66 | 14bv_amine05 |
| 67 | 14bv_amine08 |
| 68 | 14bv_amine10 |
| 69 | 14bv_amine11 |
| 70 | 14bv_amine12 |
| 71 | 14bv_amine13 |
| 72 | 14bv_amine14 |
| 73 | 14bv_amine15 |
| 74 | 14bv_amine16 |
| 75 | 14bv_amine17 |
| 76 | 14bv_amine18 |
| 77 | 14cv_amine02 |
| 78 | 14cv_amine06 |
| 79 | 14cv_amine09 |
| 80 | 14cv_amine16 |
| 81 | 14dv_amine02 |
| 82 | 14dv_amine06 |
| 83 | 14dv_amine07 |
| 84 | 14dv_amine08 |
| 85 | 14dv_amine09 |
| 86 | 14dv_amine10 |
| 87 | 14dv_amine12 |
| 88 | 14dv_amine16 |
| 89 | 14dv_amine20 |
| 90 | 14ay_amine40 |
| 91 | 14az_amine40 |
| 92 | 14ay_amine41 |
| 93 | 14az_amine41 |
| 94 | 14az_amine42 |
| 95 | 14az_amine43 |
| 96 | 14az_amine44 |
| 97 | 14az_amine45 |
| 98 | 14az_amine46 |
| 99 | 14az_amine47 |

TABLE 2

Examples of amine tails

Cyclic amine tails containing 7-member homopiperazine ring

H—N⌒NR (7-membered ring)

| | |
|---|---|
| amine01 | R = Me |
| amine02 | R = Bn |
| amine03 | R = CH$_2$4-Py |
| amine04 | R = 4-MeBn |
| amine05 | R = 4-MeOBn |
| amine06 | R = 4-iPrBn |
| amine07 | R = 4-tBuBn |
| amine08 | R = 4-BrBn |
| amine09 | R = 4-FBn |
| amine10 | R = 3-FBn |
| amine11 | R = 2-FBn |
| amine12 | R = 3,4-diFBn |
| amine13 | R = 4-ClBn |
| amine14 | R = 3-ClBn |
| amine15 | R = 2-ClBn |
| amine16 | R = 4-CF$_3$Bn |
| amine17 | R = 3-CF$_3$Bn |
| amine18 | R = 2-CF$_3$Bn |
| amine19 | R = C(=O)4-CF$_3$C$_6$H$_4$ |
| amine20 | R = (CH$_2$)$_2$4-CF$_3$C$_6$H$_4$ |

R = (α,β-unsaturated ketone with 4-Y-phenyl group)

| | |
|---|---|
| amine21 | Y = Cl |
| amine22 | Y = H |
| amine23 | Y = OMe |

Cyclic amine tails containing 6-member homopiperazine ring

H—N⌒NR (6-membered piperazine)

| | |
|---|---|
| amine24 | R = 4-CF$_3$Bn |
| amine25 | R = 4-ClBn |
| amine26 | R = Bz |
| amine27 | R = C(=O)4-CF$_3$C$_6$H$_4$ |
| amine28 | R = 3-CF$_3$Bn |
| amine29 | R = 4-FBn |
| amine30 | R = piperonyl |
| amine31 | R = 4-MeOBn |
| amine32 | R = 4-MeBn |
| amine33 | R = 4-CF$_3$C$_6$H$_4$ |
| amine34 | R = CH$_2$CH=CHCH$_2$Ph |

Linear amine tails

| | |
|---|---|
| amine35 | H—N(CH$_2$CH$_2$)N4-CF$_3$Bn |
| amine36 | H—N(CH$_2$CH$_2$)N4-CF$_3$Bn |
| amine37 | H—N(CH$_2$CH$_2$CH$_2$)N4-CF$_3$Bn |
| amine38 | H—N(CH$_2$CH$_2$CH$_2$)N4-CF$_3$Bn |

TABLE 2-continued

Examples of amine tails amine39

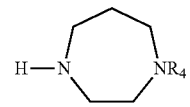

Figure 3:
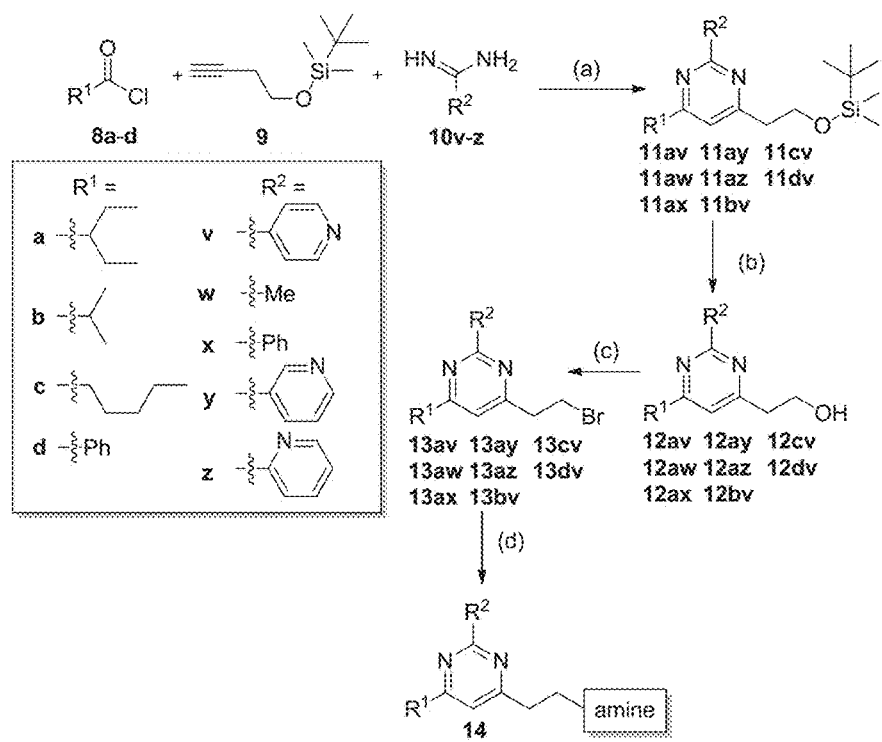
FIG. 3 shows the synthesis of 2,4,6-trisubstituted pyrimidine 14. Step (a): (i) 2 mol % Pd(PPh$_3$)$_2$Cl$_2$, 4 mol % CuI, NEt$_3$, THF, r.t. 1-2 h; (ii) Na$_2$CO$_3$, reflux 14 h; Step (b)

A general synthetic route to prepare target compound 14 is outlined in FIG. 3. In step (a), the pyrimidine head (such as 11av, 11aw, 11ax, 11ay, 11az, 11bv, 11cv, 11dv) was obtained by coupling acid chloride 8 with protected terminal alkyne 9 in the presence of an amine under Sonogashira conditions followed by addition of excess amidinium salt (such as 10v-z) one-pot, under mild conditions and in good yields.[19] $R^1$ of acid chloride 8 is selected from the group consisting of alkyl having 1-10 carbon atoms, aryl having one or two 6-membered aromatic rings, or heteroaryl having one or two 6-membered aromatic rings with at least one nitrogen (N) as the heteroatom. The amidinium salt is not limited to those illustrated. One of ordinary skill in the art would readily appreciate that other amidinium salts would also be suitable for this reaction. For example, $R^2$ may be selected from an alkyl having 1-10 carbon atoms, an aryl having one or two 6-membered aromatic rings, or a heteroaryl having one or two 6-membered aromatic rings with at least one nitrogen (N) as the heteroatom in addition to those listed in FIG. 3. The amidinium can be a hydrochloride or hydrobromide salt. The amine is selected from the group consisting of trimethylamine, N,N-diisopropylethylamine, trimethylamine, and N,N-dimethylbenzylamine.

In step (b) of FIG. 3, deprotection of the silyl group affords an alcohol (such as 12av, 12aw, 12ax, 12ay, 12az, 12bv, 12cv, 12dv), typically in quantitative yield. In one embodiment, the reagent used for deprotection of the silyl group is selected from the group consisting of concentrated hydrochloride acid in methanol, tetra-n-butylammonium fluoride (TBAF), tetra-n-butylammonium fluoride (TBAF) with acetic acid (AcOH), and potassium fluoride (KF) in tetraethylene glycol.

In step (c) of FIG. 3, the alcohol is converted into a bromide (such as 13av, 13aw, 13ax, 13ay, 13az, 13bv, 13cv, 13dv) in high yield. In one embodiment, the bromination reagent is selected from the group consisting of triphenylphosphine with carbon tetrabromide, and phosphorus tribromide with trimethylamine or pyridine. In another embodiment, the bromide is synthesized at a temperature below 50° C. In an embodiment, the bromide is freshly prepared and used immediately for the next step.

In step (d) of FIG. 3, amine-linked 2,4,6-trisubstituted pyrimidine 14 is constructed by mixing the bromide obtained in step (c) with an amine in an organic solvent. In one embodiment, the bromide is freshly prepared. In some embodiments, the amine is selected from the group consisting of homopiperazine ring 15 and $R_4$ is selected from alkyl having 1-10 carbon atoms, optionally substituted benzyl, optionally substituted phenyl, pyridylmethyl, optionally substituted benzoyl, optionally substituted phenethyl, piperonyl 3-phenyl-2-propen-1-yl, optionally substituted cinnamoyl, alkyl sulphonyl, aryl sulphonyl and heteroaryl sulphonyl. In another embodiment, the amine is selected from the group consisting of 6-member homopiperazine ring 16 and $R_5$ is selected from alkyl having 1-10 carbon atoms, optionally substituted benzyl, optionally substituted phenyl, pyridylmethyl, optionally substituted benzoyl, optionally substituted phenethyl, piperonyl, 3-phenyl-2-propen-1-yl, optionally substituted cinnamoyl, alkyl sulphonyl, aryl sulphonyl and heteroaryl sulphonyl. In one embodiment, the amine is selected from the group consisting of H—N($R_6$)—[CH$_2$]$_m$—N($R_7$)($R_8$), m is an integer selected from 2, 3, 4 and 5, and each of said $R_6$, $R_7$ and $R_8$ is independently selected from alkyl having 1-5 carbon atoms, and optionally substituted benzyl. In another embodiment, the amine is selected from the group consisting of amines listed in Table 2. One of ordinary skill in the art would readily appreciate that other amines would also undergo this reaction to give additional target compounds. In an embodiment, the organic solvent is selected from the group consisting of acetonitrile (ACN), tetrahydrofuran (THF) and diethyl ether. In another embodiment, amine-linked 2,4,6-trisubstituted pyrimidine 14 is synthesized at room temperature.

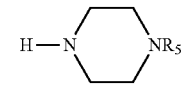

7-member homopiperazine ring 15

6-member homopiperazine ring 16

Pyrimidine 14 with a sulfonamide group is synthesized as depicted in FIG. 4. In step (a), treatment of a bromide (such as 13ay, 13az) with an amine affords a protected pyrimidine amine (such as 14ay_amine40, 14az_amine 40). In one embodiment, the amine is selected from the group consisting of 7-member homopiperazine ring 15 and 6-member homopiperazine ring 16, wherein $R_4$ and $R_5$ are Boc protecting group.

In step (b) of FIG. 4, the protected pyrimidine amine is deprotected to furnish a pyrimidine amine (such as 14ay_amine41, 14az_amine41). In one embodiment, the Boc-protected pyrimidine amine is acidified with trifluoroacetic acid (TFA) in dichloromethane (DCM).

In step (c) of FIG. 4, pyrimidine 14 with a sulfonamide group is synthesized by treating the product from step (b) with a sulfonyl chloride. In addition to those listed, the sulfonyl chloride is selected from the group consisting of methanesulfonyl chloride, p-toluenesulfonyl chloride, 4-fluorobenzenesulfonyl chloride, 1-naphthalenesulfonyl chloride, 8-quinolinesulfonyl chloride and 2-naphthalenesulfonyl chloride.

The present invention relates to a novel class of pyrimidine having a general structure (I) below:

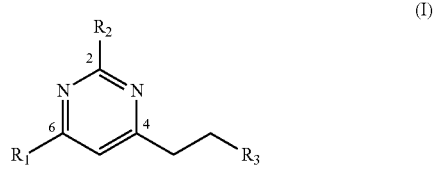

(I)

wherein $R_1$ and $R_2$ each independently represents alkyl having 1-10 carbon atoms, aryl having one or two 6-membered aromatic rings, or heteroaryl having one or two 6-membered aromatic rings with at least one nitrogen (N) as the heteroatom; and $R_3$ represents a tertiary amine —NR$_4$R$_5$;

wherein R₁ is selected from the group consisting of alkyl having 1-8 carbon atoms, phenyl and substituted phenyl;
wherein R₂ is selected from the group consisting of alkyl having 1-8 carbon atoms, phenyl, substituted phenyl, pyridin-2-yl, pyridin-3-yl and pyridin-4-yl;
wherein R₃ is

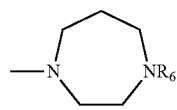

and R₆ is selected from alkyl having 1-10 carbon atoms, optionally substituted benzyl, optionally substituted phenyl, pyridylmethyl, optionally substituted benzoyl, optionally substituted phenethyl, piperonyl, 3-phenyl-2-propen-1-yl, optionally substituted cinnamoyl, alkyl sulphonyl, aryl sulphonyl and heteroaryl sulphonyl;
wherein R₃ is

and R₇ is selected from alkyl having 1-10 carbon atoms, optionally substituted benzyl, optionally substituted phenyl, pyridylmethyl, optionally substituted benzoyl, optionally substituted phenethyl, piperonyl, 3-phenyl-2-propen-1-yl, optionally substituted cinnamoyl, alkyl sulphonyl, aryl sulphonyl and heteroaryl sulphonyl;
wherein R₃ is —N(R₈)—[CH₂]$_m$—N(R₉)(R₁₀), m is an integer selected from 2, 3, 4 and 5, and each of said R₈, R₉ and R₁₀ is independently selected from alkyl having 1-5 carbon atoms, and optionally substituted benzyl.

In certain embodiments, the pyrimidine (I) is selected from the group consisting of:
1-(2-(6-phenyl-2-(pyridin-4-yl)pyrimidin-4-yl)ethyl)-4-(4-(trifluoromethyl)benzyl)-1,4-diazepane;
1-(4-isopropylbenzyl)-4-(2-(6-phenyl-2-(pyridin-4-yl)pyrimidin-4-yl)ethyl)-1,4-diazepane;
1-(2-(6-phenyl-2-(pyridin-4-yl)pyrimidin-4-yl)ethyl)-4-(4-(trifluoromethyl)phenethyl)-1,4-diazepane;
1-(4-(tert-butyl)benzyl)-4-(2-(6-phenyl-2-(pyridin-4-yl)pyrimidin-4-yl)ethyl)-1,4-diazepane;
1-(4-bromobenzyl)-4-(2-(6-phenyl-2-(pyridin-4-yl)pyrimidin-4-yl)ethyl)-1,4-diazepane;
1-(2-(6-(pentan-3-yl)-2-(pyridin-4-yl)pyrimidin-4-yl)ethyl)-4-(4-(trifluoromethyl)benzyl)-1,4-diazepane; and
1-(2-(6-(pentan-3-yl)-2-(pyridin-4-yl)pyrimidin-4-yl)ethyl)-4-(4-(trifluoromethyl)phenethyl)-1,4-diazepane.

In one embodiment, a composition comprises the novel pyrimidine (I) or its pharmaceutically acceptable salt, and a pharmaceutically acceptable carrier can be used to treat bacterial infection in a subject by administering to the subject an effective amount of the composition. In another embodiment, the infection is caused by bacteria selected from the group consisting of *Staphylococcus aureus*, Methicillin-resistant *Staphylococcus aureus* (MRSA), *Enterococcus faecalis*, *Bacillus subtilis*, *Propionibacterium acnes*, and *Clostridium difficile*. In some embodiments, the infection is caused by Gram-negative bacteria, Gram-positive bacteria or multiple drug-resistant bacteria. In certain embodiments, the infection is a skin infection, a gastrointestinal infection, a respiratory infection, urinary tract infection, or a reproductive tract infection. In one embodiment, the pyrimidine (I) is used to inhibit bacterial cell division. In another embodiment, the pyrimidine (I) inhibits Z-ring formation by filamenting temperature-sensitive mutant Z (FtsZ) protein within a bacterial cell. In one embodiment, the pyrimidine (I) binds to the guanosine triphosphate (GTP) binding site of FtsZ within a bacterial cell. In another embodiment, the composition is administered in combination with other compounds to achieve synergistic treatment of the bacterial infection. In some embodiments, the subject is a vertebrate, a mammal or human. In certain embodiments, the composition is administered orally, nasally, aurally, ocularly, sublingually, buccally, systemically, transdermally, mucosally, via cerebral spinal fluid injection, vein injection, muscle injection, peritoneal injection, subcutaneous injection, nasal or mucosal administration, or by inhalation. In a further embodiment, the composition is formulated in the form of cream, gel, ointment, suppository, tablet, granule, injection, powder, solution, suspension, spray, patch or capsule.

Minimum inhibition concentration (MIC) evaluation of the 2,4,6-trisubstituted pyrimidine 14 derivatives against *S. aureus* and *E. coli* bacterial strains identifies potent and selective anti-staphylococcal activity. Antibacterial activities of the 2,4,6-trisubstituted pyrimidine 14 derivatives are studied against clinically isolated MRSA strains. The potential for development of resistance against the compounds of the present invention is investigated, which is then followed by the evaluation of in vivo toxicity and efficacy. Binding between the compounds of the present invention and *S. aureus* FtsZ protein can be characterized by saturation transfer difference NMR. The effect of suppression on FtsZ self-polymerization can be verified by light scattering assay with purified *S. aureus* FtsZ protein. The mode of action of the antibacterial activity can be investigated by microscopic observation of a rod-shaped *B. subtilis* 168 cell morphology. Taken together, these pyrimidine derivatives represent a novel scaffold for further optimization and may have potential to be developed into a therapy for treating staphylococcal infection in the future.

The invention will be better understood by reference to the Experimental Details which follow, but those skilled in the art will readily appreciate that the specific experiments are provided only for illustrative purpose, and are not meant to limit the invention scope as described herein, which is defined by the claims following thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended, and does not exclude additional, un-recited elements or method steps.

Example 1

General Procedure for Synthesis of Pyrimidine 14

(1) Characterization of Compounds

All NMR spectra were recorded on a Bruker Advance-III spectrometer at 400.13 MHz for ¹H and 100.62 MHz for ¹³C. All NMR measurements were carried out at room temperature, and the chemical shifts are reported as parts per million (ppm) in unit relative to the resonance of CDCl₃ (7.26 ppm in the ¹H, 77.0 ppm for the central line of the triplet in the ¹³C modes, respectively). Low-resolution and high-resolution mass spectra were obtained on a Micromass Q-TOF-2 by electron spray ionization (ESI) mode. All reagents and solvents were reagent grade and were used without further purification unless otherwise stated. The plates used for thin-layer chromatography (TLC) were E. Merck Silica Gel 60F$_{254}$ (0.25 mm thickness), and they were visualized under short UV light (254 nm). Chromatographic purifications were carried out using MN silica gel 60 (230-400 mesh). Compound purity was determined by an Agilent 1100 series HPLC installed with a Prep-Sil Scalar column (4.6 mm×250 mm, 5 μm) at UV detection of 254 nm (reference at 450 nm). All tested compounds were shown to have >95% purity according to HPLC. Amine20 was prepared from homopiperazine and 1-(2-bromoethyl)-4-trifluoromethylbenzene. Amine38 was prepared from N,N-diethyl-1,3-diaminopropane and 4-(trifluoromethyl)benzyl bromide. Other amines used in this study are commercially available.

(2) General Procedure for Synthesis of Pyrimidine 11

Step (a) of FIG. 3: To a well-stirred solution of Pd(PPh$_3$)$_2$Cl$_2$ (0.4 mmol) and CuI (0.8 mmol) in degassed THF (150 mL) under nitrogen atmosphere, was added NEt$_3$ (13 mmol), acid chloride 8 (10 mmol) and alkyne 9 (10 mmol) successively. The reaction mixture was stirred for 3 h until complete conversion as monitored by TLC. Then, Na$_2$CO$_3$ (34 mmol) and amidinium hydrochloride salt 10 (12 mmol) were added to the reaction mixture. The resulting suspension was heated at reflux for 14 h. After cooling to room temperature, the reaction mixture was filtered through a short pad of silica gel to remove excess Na$_2$CO$_3$. The obtained pale brown filtrate was evaporated under reduced pressure to give a crude oil which was subjected to flash column chromatography on silica gel with gradient elution (5% EA in Hex to 30% EA in Hex) to furnish the desired product 11.

(3) General Procedure for Synthesis of Alcohol 12

Step (b) of FIG. 3: To a well-stirred solution of pyrimidine 11 (5 mmol) in methanol (20 mL) at room temperature, was added excess conc. hydrochloric acid (5 mL) dropwise. The reaction mixture was stirred for 2 h until complete conversion as monitored by TLC. Then, a 2 M NaOH solution was added to neutralize the reaction mixture (pH 7) followed by extraction with DCM. The combined organic layers were dried over MgSO$_4$, filtered and evaporated to afford the desired product 12, which is pure enough for next step.

(4) General Procedure for Synthesis of Bromide 13

Step (c) of FIG. 3: To a well-stirred solution of alcohol 12 (3 mmol) and PPh$_3$ (3.6 mmol) in THF (50 mL) at room temperature, was added carbon tetrabromide (3.6 mmol) once. The reaction mixture was stirred for 3 h until the complete conversion as monitored by TLC. The reaction mixture was filtered through a short pad of silica gel. The obtained pale brown filtrate was evaporated under reduced pressure to give a crude oil which was subjected to flash column chromatography on silica gel with gradient elution (5% EA in Hex to 20% EA in Hex) to furnish the desired product 13.

(5) General Procedure for Synthesis of Pyrimidine 14

Step (d) of FIG. 3: To a well-stirred solution of slightly excess amine (1.1 mmol) in ACN (10 mL) at room temperature, was added freshly prepared bromide 13 (1 mmol) solution in ACN (10 mL) once. The reaction mixture was stirred for 14 h until the complete conversion as monitored by TLC. The reaction mixture was evaporated under reduced pressure to give a crude oil which was subjected to flash column chromatography on silica gel with gradient elution (1% MeOH in DCM to 5% MeOH in DCM) to furnish the desired product 14.

Based on this approach, eight pyrimidine heads (FIG. 3) and thirty-nine secondary amine tails (Table 2) were designed and synthesized. As shown in Table 2, cyclic amine tails (for 7-membered homopiperazine ring, amines 01-23, and for 6-membered piperazine ring, amines 24-34) and linear amine tails (amines 35-39) were compared.

Example 2

Synthesis of 14dv_amine16

1-(2-(6-phenyl-2-(pyridin-4-yl)pyrimidin-4-yl)ethyl)-4-(4-(trifluoromethyl)benzyl)-1,4-diazepane (14dv_amine16) was prepared according to Example 1 and was obtained as a colorless oil (0.17 g, 33% yield); $^1$H NMR (400 MHz, CDCl$_3$) δ 8.77-8.82 (m, 2H), 8.40-8.44 (m, 2H), 8.20-8.24 (s, 2H), 7.64 (s, 1H), 7.52-7.58 (m, 5H), 7.45 (d, J=7.82 Hz, 2H), 3.68 (s, 2H), 3.19 (s, 4H), 2.89-3.04 (m, 4H), 2.69-2.80 (m, 4H), 1.89-1.96 (m, 2H) (FIG. 8A); $^{13}$C NMR (101 MHz, CDCl$_3$) δ 169.7, 164.1, 162.2, 150.4, 145.3, 143.4, 136.6, 131.1, 129.0, 128.9, 127.2, 125.2, 125.2, 125.1, 122.2, 115.4, 62.0, 56.9, 55.3, 54.3, 54.2, 53.8, 35.5, 27.1 (FIG. 8B); LRMS (ESI) m/z 518 (M$^+$+H, 100); HRMS (ESI) calcd for C$_{30}$H$_{31}$N$_5$F$_3$ (M$^+$+H) 518.2532, found 518.2528.

Example 3

Synthesis of 14dv_amine06

1-(4-isopropylbenzyl)-4-(2-(6-phenyl-2-(pyridin-4-yl)pyrimidin-4-yl)ethyl)-1,4-diazepane (14dv_amine06) was prepared according to Example 1 and was obtained as a colorless oil (0.12 g, 24% yield); $^1$H NMR (400 MHz, CDCl$_3$) δ 8.75-8.81 (m, 2H), 8.37-8.41 (m, 2H), 8.18-8.24 (m, 2H), 7.65 (s, 1H), 7.50-7.55 (m, 3H), 7.27-7.32 (m, J=7.82 Hz, 2H), 7.14-7.18 (m, J=7.83 Hz, 2H), 3.76 (s, 2H), 3.21-3.31 (m, 4H), 3.05-3.12 (m, 4H), 2.83-2.99 (m, 5H), 2.07-2.14 (m, 2H), 1.22 (d, J=6.85 Hz, 6H) (FIG. 9A); $^{13}$C NMR (101 MHz, CDCl$_3$) δ 168.8, 164.3, 162.2, 150.4, 148.9, 145.1, 136.4, 131.3, 129.6, 129.0, 127.3, 126.7, 122.1, 115.4, 61.8, 56.4, 53.4, 53.3, 53.0, 34.8, 33.8, 25.0, 23.9 (FIG. 9B); LRMS (ESI) m/z 492 (M$^+$+H, 100); HRMS (ESI) calcd for C$_{32}$H$_{38}$N$_5$ (M$^+$+H) 492.3127, found 492.3149.

Example 4

Synthesis of 14dv_amine20

1-(2-(6-phenyl-2-(pyridin-4-yl)pyrimidin-4-yl)ethyl)-4-(4-(trifluoromethyl)phenethyl)-1,4-diazepane (14dv_amine20) was prepared according to Example 1 and was obtained as a pale brown oil (0.14 g, 26% yield); $^1$H NMR (400 MHz, CDCl$_3$) δ 8.75 (d, J=5.87 Hz, 2H), 8.35 (d, J=5.87 Hz, 2H), 8.15-8.22 (m, 2H), 7.65 (s, 1H), 7.45-7.53 (m, 5H), 7.25 (d, J=8.31 Hz, 2H), 3.23-3.39 (m, 4H), 3.08-3.22 (m, 6H), 3.01-3.07 (m, 2H), 2.92-3.00 (m, 4H), 2.12-2.24 (m, 2H) (FIG. 10A); $^{13}$C NMR (101 MHz, CDCl$_3$) δ 168.2, 164.4, 162.2, 150.4, 145.0, 142.2, 136.2, 131.3, 129.0, 127.2, 125.5, 125.5, 125.5, 122.1, 115.4, 58.7, 56.1, 53.0, 53.0, 52.8, 34.3, 32.2, 24.2 (FIG. 10B); LRMS (ESI) m/z 532 (M$^+$+H, 100); HRMS (ESI) calcd for C$_{31}$H$_{33}$N$_5$F$_3$ (M$^+$+H) 532.2688, found 532.2676.

Example 5

Synthesis of 14dv_amine07

1-(4-(tert-butyl)benzyl)-4-(2-(6-phenyl-2-(pyridin-4-yl)pyrimidin-4-yl)ethyl)-1,4-diazepane (14dv_amine07) was prepared according to Example 1 and was obtained as a colorless oil (0.18 g, 36% yield); $^1$H NMR (400 MHz, CDCl$_3$) δ 8.75-8.79 (m, 2H), 8.35-8.39 (m, 2H), 8.18-8.23 (m, 2H), 7.66 (s, 1H), 7.50-7.55 (m, 3H), 7.32 (s, 4H), 3.83 (s, 2H), 3.27-3.40 (m, 4H), 3.12-3.22 (m, 4H), 2.95-3.09 (m, 4H), 2.20 (br. s., 2H), 1.28 (s, 9H) (FIG. 11A); $^{13}$C NMR (101 MHz, CDCl$_3$) δ 168.2, 164.4, 162.2, 151.7, 150.5, 145.0, 136.2, 131.3, 129.7, 129.1, 127.3, 125.8, 122.1, 115.4, 61.4, 56.1, 53.1, 53.0, 52.4, 34.6, 34.3, 31.3, 24.0 (FIG. 11B); LRMS (ESI) m/z 506 (M$^+$+H, 100); HRMS (ESI) calcd for C$_{33}$H$_{40}$N$_5$ (M$^+$+H) 506.3284, found 506.3281.

Example 6

Synthesis of 14dv_amine08

1-(4-bromobenzyl)-4-(2-(6-phenyl-2-(pyridin-4-yl)pyrimidin-4-yl)ethyl)-1,4-diazepane (14dv_amine08) was prepared according to Example 1 and was obtained as a pale brown oil (0.14 g, 27% yield); $^1$H NMR (400 MHz, CDCl$_3$) δ 8.80 (d, J=5.87 Hz, 2H), 8.44 (d, J=6.36 Hz, 2H), 8.20-8.24 (m, 2H), 7.62 (s, 1H), 7.53-7.58 (m, 3H), 7.39-7.44 (m, J=8.31 Hz, 2H), 7.17-7.23 (m, J=8.31 Hz, 2H), 3.57 (s, 2H), 3.09 (s, 4H) 2.89 (t, J=5.87 Hz, 2H), 2.79-2.85 (m, 2H), 2.63-2.73 (m, 4H), 1.84 (quin, J=5.87 Hz, 2H) (FIG. 12A); $^{13}$C NMR (101 MHz, CDCl$_3$) δ 170.4, 164.0, 162.2, 150.4, 145.4, 138.6, 136.8, 131.3, 131.1, 130.4, 129.0, 127.2, 122.2, 120.6, 115.4, 87.4, 61.9, 57.2, 55.2, 55.0, 54.3, 53.9, 36.1, 27.8 (FIG. 123); LRMS (ESI) m/z 529 (M$^+$+H, 100); HRMS (ESI) calcd for C$_{29}$H$_{31}$N$_5$Br (M$^+$+H) 528.1763, found 528.1762.

Example 7

Synthesis of 14av_amine16

1-(2-(6-(pentan-3-yl)-2-(pyridin-4-yl)pyrimidin-4-yl)ethyl)-4-(4-(trifluoromethyl)benzyl)-1,4-diazepane (14av_amine16) was prepared according to Example 1 and was obtained as a colorless oil (0.27 g, 53% yield); $^1$H NMR (400 MHz, CDCl$_3$) δ 8.72-8.80 (m, 2H), 8.31-8.38 (m, 2H), 7.52-7.60 (m, J=8.31 Hz, 2H), 7.40-7.49 (m, J=8.31 Hz, 2H), 6.99 (s, 1H), 3.67 (s, 2H), 2.96-3.08 (m, 4H), 2.83-2.90 (m, 2H), 2.77-2.83 (m, 2H) 2.66-2.72 (m, 4H), 2.57 (tt, J=5.81, 8.38 Hz, 1H), 1.73-1.87 (m, 6H), 0.83 (t, J=7.58 Hz, 6H) (FIG. 13A); $^{13}$C NMR (101 MHz, CDCl$_3$) δ 173.9, 169.0, 161.9, 150.3, 145.7, 143.9, 128.8, 125.6, 125.2, 125.1, 125.1, 125.1, 122.9, 122.2, 119.1, 62.2, 57.2, 55.3, 55.2, 54.3, 53.9, 51.0, 35.9, 27.8, 27.5, 12.0 (FIG. 13B); LRMS (ESI) m/z 512 (M$^+$+H, 100), 534 (M$^+$+Na, 13); HRMS (ESI) calcd for C$_{29}$H$_{37}$N$_5$F$_3$ (M$^+$+H) 512.3001, found 512.2986.

Example 8

Synthesis of 14av_amine20

1-(2-(6-(pentan-3-yl)-2-(pyridin-4-yl)pyrimidin-4-yl)ethyl)-4-(4-(trifluoromethyl)phenethyl)-1,4-diazepane (14av_amine20) was prepared according to Example 1 and was obtained as a pale brown oil (0.16 g, 30% yield); $^1$H NMR (400 MHz, CDCl$_3$) δ 8.75 (d, J=5.87 Hz, 2H), 8.30 (d, J=6.36 Hz, 2H), 7.54 (d, J=7.83 Hz, 2H), 7.31 (d, J=7.82 Hz, 2H), 7.02 (s, 1H), 3.34-3.44 (m, 2H), 3.24-3.32 (m, 2H), 3.18-2.96 (m, 10H), 2.77-2.96 (m, 2H), 2.53-2.61 (m, 1H), 2.29 (br. s., 2H), 1.72-1.83 (m, 4H), 0.81 (t, J=7.34 Hz, 6H) (FIG. 14A); $^{13}$C NMR (101 MHz, CDCl$_3$) δ 174.9, 166.3, 162.0, 150.4, 145.1, 142.0, 129.0, 125.7, 125.6, 122.1, 119.3, 58.7, 56.0, 52.9, 52.8, 52.3, 51.0, 33.6, 32.2, 27.4, 23.7, 12.0 (FIG. 14B); LRMS (ESI) m/z 526 (M$^+$+H, 100); HRMS (ESI) calcd for C$_{30}$H$_{39}$N$_5$F$_3$ (M$^+$+H) 526.3158, found 526.3177.

Example 9

Synthesis of Pyrimidine 14 with a Sulfonamide Group (1) Synthesis of Boc-Protected Pyrimidine 14az_amine40
tert-butyl-4-(2-(6-(pentan-3-yl)-2-(pyridin-2-yl)pyrimidin-4-yl)ethyl)-1,4-diazepane-1-carboxylate (14az_amine40) was prepared according to Example 1 and was obtained as a colorless oil (0.13 g, 26% yield); $^1$H NMR (400 MHz, CDCl$_3$) δ 8.78 (br. s., 1H), 8.34-8.54 (m, 1H), 7.64-7.85 (m, 1H), 7.29 (s, 3H), 6.82-7.07 (m, 1H), 3.42 (br. s., 2H), 3.35 (br. s., 2H), 2.99 (br. s., 2H), 2.87-2.95 (m, 2H), 2.57-2.72 (m, 5H), 1.62-1.83 (m, 6H), 1.38 (br. s., 9H), 0.69-0.84 (m, 6H) (FIG. 15A); $^{13}$C NMR (101 MHz, CDCl$_3$) δ 173.8, 169.3, 163.2, 155.7, 149.9, 136.6, 124.3, 123.9, 118.4, 79.1, 57.0, 55.9, 55.8, 54.7, 54.4, 50.8, 47.0, 46.5, 45.9, 45.0, 36.1, 28.4, 27.9, 27.8, 27.4, 11.9 (FIG. 15B); LRMS (ESI) m/z 454 (M$^+$+H, 100); HRMS (ESI) calcd for C$_{26}$H$_{40}$N$_5$O$_2$ (M$^+$+H) 454.3182, found 454.3164.

(2) Synthesis of Pyrimidine 14az_amine41
1-(2-(6-(pentan-3-yl)-2-(pyridin-2-yl)pyrimidin-4-yl)ethyl)-1,4-diazepane (14az_amine41): A round-bottom flask was charged with 14az_amine40 (80 mg, 0.18 mmol) and DCM (5 mL). The solution was cooled to 0° C. with an ice bath. An equal volume of TFA (5 mL) was then added dropwise, and the reaction mixture was stirred vigorously at 0° C. for 2 h. After the mixture was stirred, the reaction was quenched by pouring the mixture into a conical flask containing water. The resultant mixture was basified to pH 10 by using potassium hydroxide solution. The mixture was continuously extracted with DCM. The combined organic layers were dried over MgSO$_4$, filtered, and evaporated to give 14az_amine41 (55 mg, 88% yield) as a pale brown oil; $^1$H NMR (400 MHz, CDCl$_3$) δ 8.84 (d, J=4.89 Hz, 1H), 8.51 (d, J=7.83 Hz, 1H), 7.74-7.88 (m, 1H), 7.32-7.40 (m, 1H) 7.02 (s, 1H), 2.95-3.10 (m, 4H), 2.83-2.95 (m, 4H), 2.69-2.81 (m, 4H), 2.64 (t, J=7.09 Hz, 1H), 1.69-1.82 (m, 6H), 0.82 (t, J=7.34 Hz, 6H) (FIG. 16A); $^{13}$C NMR (101 MHz, CDCl$_3$) δ 173.8, 169.6, 163.2, 155.8, 150.0, 136.7, 124.3, 123.9, 118.4, 58.2, 57.7, 54.4, 53.4, 50.8, 49.2, 47.4, 36.2, 30.6, 27.4, 11.9 (FIG. 16B); LRMS (ESI) m/z 354 (M$^+$+H, 100), 376 (M$^+$+Na, 14); HRMS (ESI) calcd for C$_{21}$H$_{32}$N$_5$ (M$^+$+H) 354.2658, found 354.2657.

(3) Synthesis of Pyrimidine 14az_amine42
1-(methylsulfonyl)-4-(2-(6-(pentan-3-yl)-2-(pyridin-2-yl)pyrimidin-4-yl)ethyl)-1,4-diazepane (14az_amine42): A round-bottom flask was charged with 14az_amine41 (33 mg, 0.09 mmol), methanesulfonyl chloride (30 mg, 0.26 mmol), triethylamine (5 mL) and DCM (5 mL). The reaction mixture was stirred at 0° C. for 2 h. When TLC indicated complete consumption of starting material, the reaction mixture was poured into a separating funnel containing 1M hydrochloric acid solution. The mixture was continuously extracted with DCM. The combined organic layers were dried over MgSO$_4$, filtered, and evaporated to give a crude reaction mixture, which was subjected to purification by flash column chromatography on silica gel with 10-40% EA in Hex as eluent to furnish 14az_amine42 as a pale brown oil (24 mg, 60%): $^1$H NMR (400 MHz, CDCl$_3$) δ 8.84 (d, J=3.91 Hz, 1H), 8.52 (d, J=8.31 Hz, 1H), 7.83 (dt, J=1.71, 7.70 Hz, 1H), 7.36 (dd, J=5.14, 7.09 Hz, 1H), 6.99 (s, 1H), 3.31-3.46 (m, 4H), 2.98-3.07 (m, 4H), 2.76-2.87 (m, 7H), 2.55-2.69 (m, 1H), 1.86 (td, J=5.87, 11.74 Hz, 2H), 1.70-1.82 (m, 4H), 0.83 (t, J=7.34 Hz, 6H) (FIG. 17A); $^{13}$C NMR (101 MHz, CDCl$_3$) δ 174.0, 169.1, 163.3, 155.7, 150.0, 136.7, 124.4, 124.0, 118.4, 57.2, 56.2, 54.1, 50.8, 48.5, 46.9, 37.2, 36.1, 28.5, 27.4, 11.9 (FIG. 17B); LRMS (ESI) m/z 432 (M$^+$+H, 100); HRMS (ESI) calcd for C$_{22}$H$_{34}$N$_5$O$_2$S (M$^+$+H) 432.2433, found 432.2446.

Example 10

Evaluation of Antimicrobial Activities and SAR Study

This example illustrates the evaluation of 2,4,6-trisubstituted pyrimidines 14 for their antimicrobial activities against the Gram positive *S. aureus* strain ATCC29213 and the Gram negative *E. coli* strain ATCC25922 by measuring their MIC, which is the lowest concentration of an antimicrobial agent that prevents visible growth of a microorganism in a broth dilution susceptibility test according to the standard method approved by the Clinical and Laboratory Standards Institute (CLSI) guidelines.[21]

Procedure of Antimicrobial susceptibility test: The MIC value of compounds was measured in the antimicrobial susceptibility test using the broth microdilution procedure in accordance with the CLSI guidelines.[21] Cation-adjusted Mueller Hinton broth (CA-MHB) was used for all the *S. aureus* strains in the assay. Cells in exponential phase of growth were diluted to approximately $5 \times 10^5$ cfu/mL. Stock solutions of each compound were freshly dissolved in dimethyl sulfoxide (DMSO). Then, serial dilutions of each compound in CA-MHB medium were added into 96-well microplate. The final percentage of DMSO in the assay was 1%. Control experiments were performed with 1% DMSO instead of the compound solution. After being incubated at 37° C. for 18 h, $OD_{600}$ value of cells was measured on a microplate reader and the percentage of bacterial cell inhibition with respect to controls was calculated. The MIC value was defined as the lowest compound concentration at which the growth of bacteria was inhibited by ≥90%. Three independent assays were performed for each compound.

Figure 1:
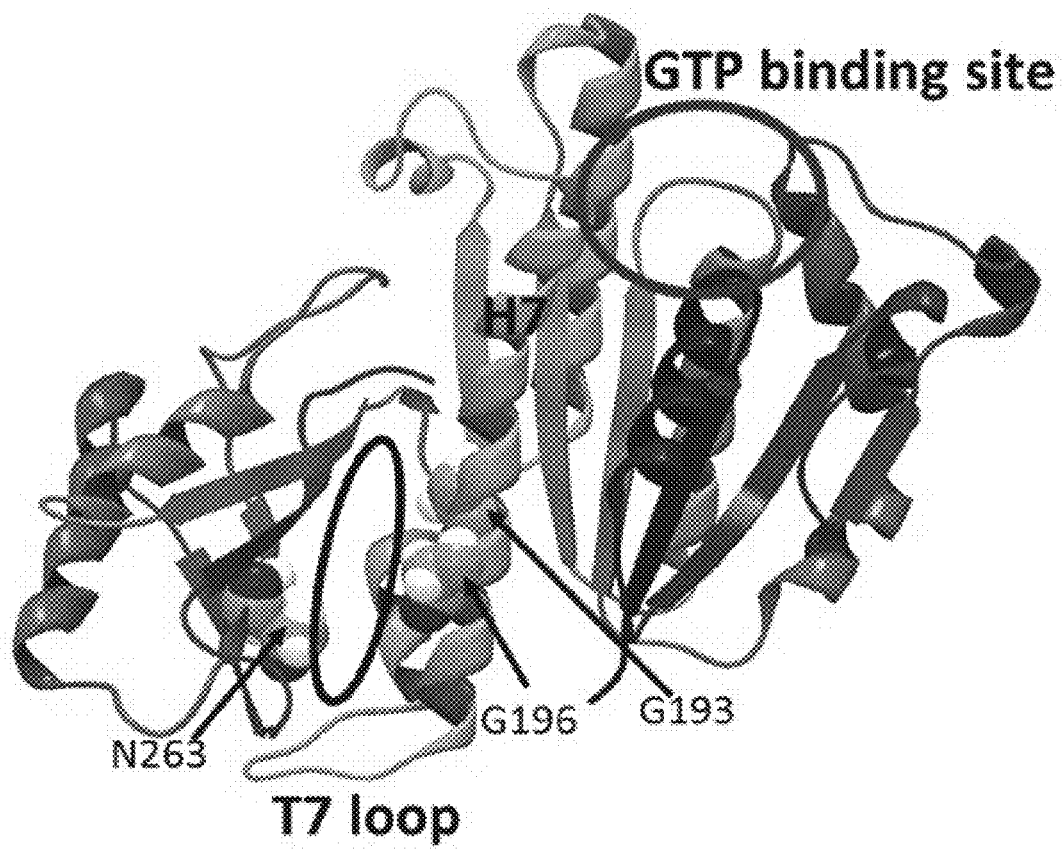
FIG. 1 shows a crystal structure of *S. aureus* FtsZ (PDB ID: 4DXD) with labeled GTP binding site, T7 loop, H7 helix and amino acids at positions 193, 196 and 263.

Results: Parent compound 7b (FIG. 1, bottom right) was selected as positive control for comparison purpose. Compound 7b inhibited the growth of both bacterial strains with MIC at 125 μM, demonstrating moderate antibacterial activity and no selectivity of killing between two bacterial strains (Table 3, Entry 1). In contrast, some compounds of the present invention display superior antimicrobial activity and selectivity. The MIC screening results are summarized in Table 3, in which compounds with MIC values against *S. aureus* less than 20 μM are shown in Entries 1-23. In general, among the newly synthesized compounds, most of them displayed potent inhibitory activities against the growth of *S. aureus* but not *E. coli* at a concentration of 125 μM. The weak activity against *E. coli* may be attributed to their poor penetration ability into the cytoplasm of Gram negative bacteria, which have an outer membrane of low permeability. For compounds listed in Table 3, seven compounds displaying superior potency (MIC at 5-8 μM) and selectivity (>15) were identified, namely 14dv_amine16, 14dv_amine06, 14dv_amine20, 14dv_amine07, 14dv_amine08, 14av_amine16 and 14av_amine20 (Table 3, Entry 2-8). Compared with compound 7b (Entry 1), their potency was improved by 15 to 25-fold and their selectivity by >15-fold. Interestingly, these compounds possess the common structural features of a 4-pyridyl (4-Py) group at position 2 and a cyclic 7-membered homopiperazine ring substituted with a benzyl group at position 4. Detailed SAR analysis of 2,4,6-trisubstituted pyrimidines 14 derivatives are depicted in FIG. 5. For the pyrimidine head, 4-pyridyl group of $R^2$ of 14av_amine16 was very important for potent antibacterial activity. Replacing this function group with others such as the 3-pyridyl of 14ay_amine16, 2-pyridyl of 14az_amine16, phenyl of 14ax_amine16 and methyl groups of 14aw_amine16 resulted in weak antibacterial activity, implying that nitrogen atom of 4-Py group is crucial for maintaining potent antibacterial activity. For $R^1$ group of pyrimidine head, both phenyl of 14dv_amine16 and 3-pentyl group of 14av_amine16 were favorable substituents. Less bulky iso-propyl group of 14bv_amine16 and linear n-pentyl group of 14cv_amine16 both caused poor antibacterial activity. In general, pyrimidine head bearing 4-pyridyl group of $R^2$ and phenyl or 3-pentyl groups of $R^1$ exhibited the most potent antibacterial activity. For SAR analysis of the amine tail (14av_amine01-14av_amine39), there were two important structural features that gave rise to potent antibacterial activity: (1) cyclic 7-member homopiperazine ring with substituted benzyl group; (2) the benzyl group substituted with a bulky group (tert-butyl, trifluoromethyl, iso-propyl, bromo) at para-position. Replacing the amine tail with cyclic 6-member piperazine ring of 14av_amine24, linear 1,2-diamine of 14av_amine35-36 or 1,3-diamine of 14av_amine37-38 resulted in poor antibacterial activity. It was also worthy to note that replacing the benzylic carbon with a rigid functional group, such as carbonyl group of 14av_amine19, sulfonyl group of 14az_amine43-44 or α,β-unsaturated ketone group of 14av_amine21-23, caused poor antibacterial activity. These results suggested that a more flexible and freely rotatable functional group should be installed at this position. This observation was further supported by the low MIC value of compound 14av_amine20, in which the benzylic carbon was replaced with a freely rotatable $CH_2CH_2$ group.

TABLE 3

MIC values of 2,4,6-trisubstituted pyrimidines against *S. aureus* 29213 and *E. coli* ATCC 25922 as well as calculated selectivity index ($MIC^c/MIC^b$).

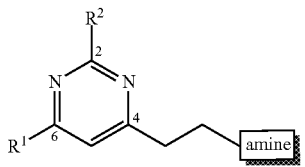

14

| Entry | Compound No. | $R^1$ | $R^2$ | Amine No. | $MIC^b$ | $MIC^c$ | $MIC^c/MIC^b$ |
|---|---|---|---|---|---|---|---|
| 1 | 7 | N.A. | N.A. | N.A. | 125 | 125 | 1 |
| 2 | 14dv_amine16 | phenyl | 4-Py | 16 | 5 | >125 | >25 |
| 3 | 14dv_amine06 | phenyl | 4-Py | 06 | 5 | >125 | >25 |

TABLE 3-continued

MIC values of 2,4,6-trisubstituted pyrimidines against *S. aureus* 29213 and *E. coli* ATCC 25922 as well as calculated selectivity index (MIC$^c$/MIC$^b$).

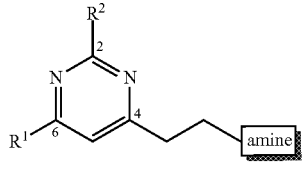

14

| Entry | Compound No. | R$^1$ | R$^2$ | Amine No. | MIC$^b$ | MIC$^c$ | MIC$^c$/MIC$^b$ |
|---|---|---|---|---|---|---|---|
| 4 | 14dv_amine20 | phenyl | 4-Py | 20 | 5 | >125 | >25 |
| 5 | 14dv_amine07 | phenyl | 4-Py | 07 | 5 | >125 | >25 |
| 6 | 14dv_amine08 | phenyl | 4-Py | 08 | 5 | >125 | >25 |
| 7 | 14av_amine16 | 3-pentyl | 4-Py | 16 | 8 | >125 | >15 |
| 8 | 14av_amine20 | 3-pentyl | 4-Py | 20 | 8 | >125 | >15 |
| 9 | 14cv_amine06 | n-pentyl | 4-Py | 06 | 10 | >125 | >12 |
| 10 | 14cv_amine16 | n-pentyl | 4-Py | 16 | 10 | >125 | >12 |
| 11 | 14dv_amine12 | phenyl | 4-Py | 12 | 10 | >125 | >12 |
| 12 | 14dv_amine10 | phenyl | 4-Py | 10 | 10 | >125 | >12 |
| 13 | 14av_amine28 | 3-pentyl | 4-Py | 28 | 10 | >125 | >12 |
| 14 | 14av_amine38 | 3-pentyl | 4-Py | 38 | 10 | >125 | >12 |
| 15 | 14av_amine39 | 3-pentyl | 4-Py | 39 | 10 | >125 | >12 |
| 16 | 14av_amine24 | 3-pentyl | 4-Py | 24 | 12 | >125 | >10 |
| 17 | 14av_amine35 | 3-pentyl | 4-Py | 35 | 12 | >125 | >10 |
| 18 | 14av_amine13 | 3-pentyl | 4-Py | 13 | 13 | >125 | >9 |
| 19 | 14av_amine06 | 3-pentyl | 4-Py | 06 | 16 | >125 | >7 |
| 20 | 14av_amine07 | 3-pentyl | 4-Py | 07 | 16 | >125 | >7 |
| 21 | 14av_amine08 | 3-pentyl | 4-Py | 08 | 16 | >125 | >7 |
| 22 | 14av_amine17 | 3-pentyl | 4-Py | 17 | 16 | >125 | >7 |
| 23 | 14av_amine18 | 3-pentyl | 4-Py | 18 | 16 | >125 | >7 |

N.A.: not applicable.
MIC$^b$: Minimum inhibitory concentration in uM against *S. aureus*
MIC$^c$: Minimum inhibitory concentration in uM against *E. coli*
MIC$^c$/MIC$^b$: Selectivity index Example 11

Antibacterial Activity Against Drug-Resistant *S. aureus* Strains

Procedure for expression and purification of *S. aureus* FtsZ protein: *S. aureus* FtsZ protein was prepared as previous reported.[16a] In brief, *E. coli* BL21(DE3) cells, transformed with a pRSET-A-S vector carrying *S. aureus* FtsZ with a 6-histidine tag attached, were streaked on a nutrient agar plate containing 50 μg/mL ampicillin. After overnight incubation at 37° C., a single colony was inoculated into 5 mL of Luria-Bertani (LB) medium in the presence of 50 μg/mL ampicillin, which was then incubated at 37° C., with shaking at 250 rpm for 16 h. The overnight culture was transferred into a fresh 2×TY medium in a dilution ratio of 1:100 and 50 μg/mL ampicillin was then added, followed by incubation at 37° C. with shaking at 250 rpm. When OD$_{600}$ reached 0.8, protein expression was induced with 0.4 mM isopropyl-β-D-thiogalactopyranoside (IPTG) for 4 h. Cells were harvested by centrifugation at 9000 rpm for 20 min at 4° C. The cell pellet was resuspended in 20 mL of solubilization buffer (50 mM Tris-HCl, 150 mM NaCl, 1 mM PMSF and 1 mM EDTA, pH 7.4) and then lysed with 1 mg/mL of lysozyme. The mixture was incubated for 1 h on ice. The cells were disrupted by sonication and the crude lysate obtained was centrifuged at 13,000 rpm for 1 h at 4° C. The supernatant containing 6-histidine tagged *S. aureus* FtsZ was collected and loaded onto a nickel charged HiTrap chelating column pre-equilibrated with starting buffer (20 mM sodium phosphate buffer, 0.5 M NaCl, pH 7.4). The column was then washed with 8 column volumes of the starting buffer to remove the unbound proteins, and the histidine-tagged enzyme was eluted by a linear gradient of 0-0.2 M imidazole. Fractions containing *S. aureus* FtsZ were pooled, buffer-exchanged with 20 mM NH$_4$HCO$_3$ (pH 8.0) at 4° C., lyophilized, and stored at −20° C. A stock solution of *S. aureus* FtsZ for the subsequent Saturation Transfer Difference (STD) NMR study and light scattering assay and GTPase activity assay was prepared from the lyophilized powder.

Results: Three compounds, namely 14av_amine16, 14dv_amine16 and 14dv_amine06, were selected to be tested against nine in-house clinically isolated bacterial strains including *S. aureus* ATCC29247, which is an ampicillin resistant strain, *S. aureus* ATCC BAA-41, ATCC BAA-1717, ATCC BAA-1720, ATCC 43300 which are methicillin resistant strains and four USA300 strains, (#417, #757, #1799 and #2690), which are the predominant strain type of community-associated MRSA strains in the United States. MIC screening results are summarized in Table 4. All compounds were found to retain potent antibacterial activities against these antibiotic-resistant strains with MIC values ranging from 5 to 12 μM. Compound 14dv_amine16 and 14dv_amine06 displayed the most potent antibacterial activity against *S. aureus* ATCC 29247 and ATCC BAA-1717, with MIC at 5 μM. Compared with methicillin, which is the clinically used antibiotic with MIC values higher than 30 μM against most of the MRSA, these pyrimidine derivatives exhibited significantly lower MIC values and thus the potential to be developed into new anti-staphylococcal agents in the future. It was worthy to mention that compounds 7 did not exhibit any antibacterial activity against these clinically isolated *S. aureus* strains (MIC>100 μM).

TABLE 4

MIC values of selected pyrimidines against nine clinically isolated *S. aureus* strains.

| | MIC (μM) | | | | | | | | |
|---|---|---|---|---|---|---|---|---|---|
| Compound No. | Strain 1 | Strain 2 | Strain 3 | Strain 4 | Strain 5 | Strain 6 | Strain 7 | Strain 8 | Strain 9 |
| 14av_amine16 | 8 | 8 | 12 | 12 | 12 | 12 | 12 | 12 | 12 |
| 14dv_amine16 | 5 | 5 | 10 | 10 | 10 | 10 | 10 | 10 | 10 |
| 14dv_amine06 | 5 | 5 | 10 | 10 | 10 | 10 | 10 | 10 | 10 |
| Methicillin | N.D. | >30 | >30 | >30 | >30 | >30 | 30 | 30 | 15 |

N.D.: not determined; Strain 1: ATCC 29247; Strain 2: ATCC BAA-1717; Strain 3: ATCC BAA-1720; Strain 4: ATCC BAA-41; Strain 5: ATCC 43300; Strain 6: USA300 #417; Strain 7: USA300 #757; Strain 8: USA300 #1799; Strain 9: USA300 #2690.

Example 12

Investigation of Potential for Development of Resistance and In Vivo Biological Evaluation This example evaluates the spontaneous resistance rate of compounds in MRSA and measures the in vivo toxicity and efficacy.

a) Frequency of Resistance (FOR) Determination

Procedure: MRSA ATCC 43300 cells were grown to late-exponential phase ($1 \times 10^9$ CFU/mL) and spread on agars plates containing 1% DMSO or compound 14av_amine16 at 8 folds of MIC level. The plates were incubated for 48 hours to allow resistant mutants to grow. The spontaneous FOR was calculated as the number of resistance colonies divided by the number of CFUs originally plated. The assay was performed in triplicates.

Results: As shown in FIG. 18A (left), almost confluent bacterial growth was observed for DMSO treated bacterial cells yet no colony was observed for plates treated with compound 14av_amine16 (FIG. 18A, right) after 48 hours' incubation, implying that the rate of emergence of spontaneous resistant mutants was as low as $<1 \times 10^9$. This finding confirmed that the chance of occurrence of mutational changes and confer resistance to inhibitors acting on GTP binding site of FtsZ protein is extremely low. This low frequency of spontaneous resistance implies a reduced probability of rapid development of resistance against compound 14av_amine16 in clinical practice.

b) Evaluation of the Toxicity and Antimicrobial Efficacy Using a *G. Mellonella* Model of Infection Procedure: Compound 14av_amine16 was tested in a *Galleria mellonella* model, which are an easy and inexpensive in vivo model with no ethical constraints for investigating antibacterial activity of a compound.[22] The *G. mellonella* model of *S. aureus* infection was used as previously described.[24] Briefly, 1 mL aliquots of overnight cultures of *S. aureus* 43300 were pelleted by centrifugation and washed with sterile PBS before being resuspended in 100 μL of PBS. *G. mellonella* larvae (N=10) that weighed 200-300 mg were then inoculated with 10 μL of *S. aureus* ($2.5 \times 10^6$ CFU) into the last left proleg. Larvae were then treated with compounds at 1 h before bacterial inoculation. Treatments were performed in the same manner as infection, except that compounds were injected into the next left proleg moving toward the head of the larvae. Larvae were then incubated at 37° C. and mortality rates were monitored at 12 h interval for 48 h; larvae were considered dead if they did not respond to physical stimuli. Data was analyzed for statistical significance using a log rank and $\chi$ square test with 1 degree of freedom. Various concentrations of compound 14av_amine16 dissolved in 50% PEG in saline (0 mg/Kg, 50 mg/Kg and 100 mg/Kg) were injected into the hemocoel of last-instar *G. mellonella* larvae and survival was scored over time.

To examine the feasibility of using *G. mellonella* for compound 14av_amine16 toxicity study, the ability of compound 14av_amine16 to kill *G. mellonella* larvae was examined.

The efficacy of compound 14av_amine16 against *G. mellonella* larvae infected with MRSA ATCC 43300 was investigated. Inoculation of lethal dose of $2.5 \times 10^6$ CFU/larva of MRSA ATCC 43300 led to a significant death rate. All larvae injected with 50% PEG in saline (0 mg/Kg) died within a 24 hours' infection period.

Results: All concentrations of compound 14av_amine16 tested did not kill *G. mellonella* larvae during a 48-hours period (FIG. 18B). These data indicate that formulation of 50% PEG in saline and compound 14av_amine16 are non-toxic and safe against *G. mellonella* larvae.

Injection of compound 14av_amine16 at doses of 50 mg/Kg to infected larvae was found to prolong the survival time of infected larvae to 36 hours (FIG. 18C). It is observed that 20% survival rate of infected larvae over the infection period with increased dosing with 14av_amine16 at 100 mg/Kg. Compared to the vehicle group, it was found to be highly significant ($p<0.05$). Further increased dosing did not lead to improved efficacy (Data not shown). These data indicated that compound 14av_amine16 is capable of preventing or delaying the lethal effect of MRSA ATCC 43300 in *G. mellonella* larvae.

Example 13

Saturation Transfer Difference (STD) NMR Study

Procedure STD NMR study: STD NMR experiments were performed on a Bruker Avance III 600 NMR spectrometer equipped with a QCI cryoprobe at 298K. Spectra were recorded with a carrier set at 0.5 ppm for on-resonance irradiation and 30 ppm for off-resonance irradiation. Control spectra were recorded under identical conditions without compound to test for artifacts. Selective protein saturation was accomplished using a train of 40 Gauss-shaped pulses (50 ms with 1 ms delay between pulses) for a total saturation time of 2 s at an experimentally determined optimal power (7.7625 W on the probe); a T1ρ spinlock filter (20-50 ms) was incorporated to suppress protein resonances. STD spectra were recorded using a minimum of 128 scans and 32 k points covering a spectral width of 6600 Hz. The free induced decay (FID) was multiplied by an exponential line-boarding function of 1 Hz and zero-filled by a factor of two prior to Fourier transformation. On- and off-resonance spectra were processed independently and subtracted to provide a difference spectrum. Spectra processing was performed using Topspin software (Bruker). Group epitope mapping were performed by integrated the STD signal of the individual protons with respect to the strongest STD signal, which was assigned to a value of 100%.

Results: STD NMR spectroscopy is a powerful and unique tool that can detect the magnetization that was transferred from a protein to a bound ligand proton. It is commonly used to detect binding of low molecular weight compound to large biomolecules.[23] In order to get further insights of the interaction between compounds 14av_amine16 and S. aureus FtsZ protein, STD NMR spectroscopy is employed to characterize the binding properties and identify epitopes of small molecules that bind to a protein receptor. S. aureus FtsZ protein was expressed and purified as described in a previous reported.[16a] STD NMR spectroscopy was performed and the relative degrees of saturation for individual protons of compound 14av_amine16 are displayed in FIG. 6 with the integral value of the largest signal set to 100%. The line boarding observed is caused by compound 14av_amine16 being in close contact with the FtsZ protein, resulting in slow tumbling rate of the protein-ligand complex, which also confirmed that compound 14av_amine16 indeed bind to FtsZ protein. All of the protons of compound 14av_amine16 showed some degree of enhancement, demonstrating that the molecule, except the homopiperazine moiety, is bound in the active site of FtsZ protein. The largest amount of saturation transfer was observed for H1, indicating the pyrimidine ring of compound 14av_amine16 are making more intimate contacts with the active site residue of FtsZ protein.

Example 14

S. Aureus FtsZ Polymerization and GTPase Hydrolysis Assay

This example determines whether the binding of compound 14av_amine16 to S. aureus FtsZ protein led to a change in the polymerization activity and GTPase activity of the protein itself.

a) S. Aureus FtsZ Polymerization Assay

Procedure: The polymerization of recombinant S. aureus FtsZ was measured using a 90° light scattering in a thermostatically (37° C.) controlled Fluorescence Spectrometer LS 50B according to previous reports.[16a,19] Both excitation and emission wavelengths were fixed to 600 nm with a slit width of 2.5 nm. S. aureus FtsZ (12.5 µM) in 50 mM 4-morpholinepropanesulfonic acid (MOPS) buffer (pH 6.5) was incubated with DMSO or different concentrations of compound for 10 min at 25° C. Then, 50 mM KCl and 10 mM MgCl$_2$ were added to establish a baseline. After 8 min, the final concentration of 1 mM GTP was added at the last fraction and the increase in light scattering measured for an additional 2000 seconds. The rate and extent of polymerization were measured. Appropriate blanks were subtracted from all experimental data. Results shown are the average of three independent experiments.

Results: To assay this function, an in vitro light scattering assay, in which FtsZ polymerization was detected in solution by a time-dependent increase in light scattering as reflected by an increase in solution absorbance at 600 nm, was employed. FIG. 7 shows the relative time-dependence absorbance at 600 nm of S. aureus FtsZ in the presence of 14av_amine16 at concentrations ranging from 0 to 30 µM. It was clearly demonstrated that 14av_amine16 potently suppresses the self-polymerization of S. aureus FtsZ protein with the magnitude of these suppressing effects increasing with increasing compound concentration. Complete inhibition of FtsZ polymerization was observed at 30 µm of 14av_amine16. These results suggested that 14av_amine16 inhibits the proliferation of S. aureus via suppressing the self-polymerization of FtsZ protein.

b) GTPase Hydrolysis Assay

Procedure: The inhibitory effect of compound 14av_amine16 on GTPase hydrolysis activity was investigated according to the protocol described previously.[18] The GTPase activity of S. aureus FtsZ was estimated in a 96-well microplate using a CytoPhos phosphate assay Biochem Kit based on the manufacturer's instructions. Purified S. aureus FtsZ (7.5 µM) was incubated with serial dilutions of compound in 50 mM 4-morpholinepropanesulfonic acid (MOPS, pH 6.5) buffer at 25° C. for 10 minutes. 1% DMSO was used for control experiment. Then 5 mM of MgCl$_2$ and 200 mM of KCl were added followed by addition of 500 µM GTP and incubation at 37° C. After half an hour, the reactions were quenched by adding 100 µL of Cytophos reagent. The precipitated inorganic phosphate was quantified by measuring the absorbance at 650 nm in a microplate reader. Three independent assays were performed in triplicate.

Results: Compounds 7a and 7b inhibited the GTPase hydrolysis activity with IC$_{50}$ at 73 µM and 189 µM respectively. However, compound 14av_amine16 at 50 µM and 75 µM displayed only moderate inhibition of the GTPase hydrolysis activity at about 20±3% and 25±4% respectively. GTPase hydrolysis activity at higher compound concentration (>80 µM) cannot be measured due to poor compound solubility, which causes precipitation in aqueous medium. Nonetheless, it seems very likely that compound 14av_amine16 suppresses the self-polymerization of FtsZ protein, probably via disrupting the GTPase hydrolysis activity of FtsZ protein.

Example 15

Effects on the B. Subtilis 168 Cell Morphology and Localization of the Z-Ring

This example investigates the underlying mode of action of the antibacterial activity of compound 14av_amine16 by microscopic observation of a rod-shaped B. subtilis 168 cell morphology.

a) Bacterial Morphology of B. subtilis 168

Procedure: The B. subtilis 168 cells were grown in LB medium. The cultures at an A$_{600}$ of 0.01 from an overnight culture were inoculated in the same medium containing different concentrations of the test compounds and grown at 37° C. for 4 h. The cells for morphology studies were harvested and resuspended in 100 µL of PBS buffer containing 0.25% agarose. 10 µL of the suspension mixture were then placed on a microscopic slide pretreated with 0.1% (w/v) poly-L-lysine and the morphology of the bacterial cells was observed under a phase-contrast optical microscope at 40× magnification. The images were captured using an Olympus Bio Imaging Navigator FSX 100 microscope.

Results: Compound 14av_amine16 exhibited antibacterial activity against B. subtilis 168 with MIC value at 12 µM. Treatment of B. subtilis cell at a sub-lethal concentration of compound 14av_amine16 significantly increased the cell length with average cell length>20 μm (FIG. 19B) as compared with the DMSO treated cells (cell length<5 μm, FIG. 19A). Interestingly, such phenomenon of cell elongation was also observed for other FtsZ inhibitors reported, strongly suggesting that 14av_amine16 interacts with FtsZ protein in vivo. The iconic filamentous cell phenotype of FtsZ inhibitors was believed to be caused by the disruption and mislocalization of the Z-ring.

b) Z-Ring Visualization of *B. Subtilis* 168

Procedure: A single colony of FtsZ GFP fusion stain of *B. subtilis* 168 was grown in 5 ml 2×TY medium with 35 mg/L chloramphenicol for 14 hours at 30° C. An overnight culture was then diluted to an $OD_{600}$ of 0.01 by 2×TY medium containing the absence (DMSO) and presence of 6 μM test compounds and 40 μM of IPTG, it grew at 30° C. after 4 hours of incubation; the cells were pelleted and re-suspended in 300 μL PBS buffer containing 1% agarose. 10 μL suspensions were then placed on the microscopic slide. The morphology of bacterial cell was observed under a fluorescent and phase-contrast microscope at 40× magnification, using the software of Olympus FSX100® Bio Imaging Navigator to capture images.

Results: A fluorescence microscopic analysis of dynamic Z-ring formation in *B. subtilis* 168 was carried out by using a functional green fluorescent protein tagged FtsZ in *B. subtilis* 168. In the absence of compound (DMSO treated), fluorescent foci corresponding to Z-ring formation were observed at mid-cell. Each cell possesses only one fluorescent focus, indicating the proper Z-ring formation and localization (FIG. 19C, white arrow). In contrast, upon exposure to compound 14av_amine16, bacteria cell lacked mid-cell foci. Instead, FtsZ protein was randomly distributed as discrete multiple foci (FIG. 19E, white arrows) throughout the whole elongated cell, demonstrating that compound 14av_amine16 caused obvious mislocalization of the Z-ring.

In summary, a new class of amine-linked 2,4,6-trisubstituted pyrimidines with potent anti-staphylococcal activity was discovered. SAR studies of these compounds identified seven compounds possessing potent and selective anti-staphylococcal activity with MIC values of 5 μM. These compounds exhibited potent antibacterial activities against clinically isolated MRSA strains. These promising results led to efficacy testing of 14av_amine16, which revealed a very low spontaneous frequency of resistance and limited toxicity against *G. mellonella* larvae. Investigation of the mode of action suggests that compound 14av_amine16 exerted its antibacterial activity by suppressing FtsZ polymerization, resulting in obvious mislocalization of the Z-ring formation. The observed potency makes the 2,4,6-trisubstituted pyrimidines of the present invention excellent anti-staphylococcal agents.

REFERENCES

[1] Klevens, R.; Morrison, M. A.; Nadle, J.; et al., INvasive methicillin-resistant *staphylococcus aureus* infections in the united states. *JAMA* 2007, 298 (15), 1763-1771.

[2] http://www.cdc.gov/drugresistance/pdf/ar-threats-2013-508.pdf (accessed Feb. 5, 2016).

[3] Lock, R. L.; Harry, E. J., Cell-division inhibitors: new insights for future antibiotics. *Nat. Rev. Drug Discov.* 2008, 7 (4), 324-338.

[4] (a) Sass, P.; Brotz-Oesterhelt, H., Bacterial cell division as a target for new antibiotics. *Curr. Opin. Microbiol.* 2013, 16 (5), 522-530; (b) Foss, M. H.; Eun, Y.-J.; Weibel, D. B., Chemical-Biological Studies of Subcellular Organization in Bacteria. *Biochemistry* 2011, 50 (36), 7719-7734; (c) Schaffner-Barbero, C.; Martín-Fontecha, M.; Chacón, P.; Andreu, J. M., Targeting the Assembly of Bacterial Cell Division Protein FtsZ with Small Molecules. *ACS Chem. Biol.* 2012, 7 (2), 269-277; (d) Ma, S.; Ma, S., The Development of FtsZ Inhibitors as Potential Antibacterial Agents. *ChemMedChem* 2012, 7 (7), 1161-1172; (e) Ojima, I.; Kumar, K.; Awasthi, D.; Vineberg, J. G., Drug discovery targeting cell division proteins, microtubules and FtsZ. *Bioorganic Med. Chem.* 2014, 22 (18), 5060-5077; (f) Hurley, K. A.; Santos, T. M. A.; Nepomuceno, G. M.; Huynh, V.; Shaw, J. T.; Weibel, D. B., Targeting the bacterial division protein FtsZ. *J. Med. Chem.* 2016, DOI: 10.1.021/acs.jmedchem.5b01098.

[5] Li, Y.; Hsin, J.; Zhao, L. Y.; Cheng, Y. W.; Shang, W. N.; Huang, K. C.; Wang, H. W.; Ye, S., FtsZ Protofilaments Use a Hinge-Opening Mechanism for Constrictive Force Generation. *Science* 2013, 341 (6144), 392-395.

[6] Matsui, T.; Han, X. R.; Yu, J.; Yao, M.; Tanaka, I., Structural Change in FtsZ Induced by Intermolecular Interactions between Bound GTP and the T7 Loop. *J. Biol. Chem.* 2014, 289 (6), 3501-3509.

[7] (a) Haydon, D. J.; Stokes, N. R.; Ure, R.; Galbraith, G.; Bennett, J. M.; Brown, D. R.; Baker, P. J.; Barynin, V. V.; Rice, D. W.; Sedelnikova, S. E.; Heal, J. R.; Sheridan, J. M.; Aiwale, S. T.; Chauhan, P. K.; Srivastava, A.; Taneja, A.; Collins, I.; Errington, J.; Czaplewski, L. G., An inhibitor of FtsZ with potent and selective anti-staphylococcal activity. *Science* 2008, 321 (5896), 1673-1675; (b) Haydon, D. J.; Bennett, J. M.; Brown, D.; Collins, I.; Galbraith, G.; Lancett, P.; Macdonald, R.; Stokes, N. R.; Chauhan, P. K.; Sutariya, J. K.; Nayal, N.; Srivastava, A.; Beanland, J.; Hall, R.; Henstock, V.; Noula, C.; Rockley, C.; Czaplewski, L., Creating an Antibacterial with in Vivo Efficacy: Synthesis and Characterization of Potent Inhibitors of the Bacterial Cell Division Protein FtsZ with Improved Pharmaceutical Properties. *J. Med. Chem.* 2010, 53 (10), 3927-3936; (c) Qiang, S.; Wang, C.; Venter, H.; Li, X.; Wang, Y.; Guo, L.; Ma, R.; Ma, S., Synthesis and Biological Evaluation of Novel FtsZ-targeted 3-arylalkoxy-2,6-difluorobenzamides as Potential Antimicrobial Agents. *Chem. Biol. Drug Des.* 2016, 87, 257-264.

[8] Kaul, M.; Mark, L.; Zhang, Y. Z.; Parhi, A. K.; LaVoie, E. J.; Pilch, D. S., An FtsZ-Targeting Prodrug with Oral Antistaphylococcal Efficacy In Vivo. *Antimicrob. Agents Chemother.* 2013, 57 (12), 5860-5869.

[9] (a) Kaul, M.; Mark, L.; Zhang, Y. Z.; Parhi, A. K.; LaVoie, E. J.; Pilch, D. S., Pharmacokinetics and in vivo antistaphylococcal efficacy of TXY541, a 1-methylpiperidine-4-carboxamide prodrug of PC190723. *Biochem. Pharmacol.* 2013, 86 (12), 1699-1707; (b) Kate, M.; Mark L.; Zhang, Y. Z.; Parhi, A. K.; Lyu, Y. L.; Pawlak, J.; Saravolatz, S.; Saravolatz, L. D.; Weinstein, M. P.; LaVoie, E. J.; Pilch, D. S., TXA709, an FtsZ-Targeting Benzamide Prodrug with Improved Pharmacokinetics and Enhanced In Vivo Efficacy against Methicillin-Resistant *Staphylococcus aureus*. *Antimicrob. Agents Chemother.* 2015, 59 (8), 4845-4855; (c) Lepak, A. J.; Parhi, A.; Madison, M.; Marchillo, K.; VanHecker, J.; Andes, D. R., In Vivo Pharmacodynamic Evaluation of an FtsZ Inhibitor, TXA-709, and Its Active Metabolite, TXA-707, in a Murine Neutropenic Thigh Infection Model. *Antimicrob. Agents Chemother.* 2015, 59 (10), 6568-6574.

[10] Stokes, N. R.; Baker, N.; Bennett, J. M.; Berry, J.; Collins, I.; Czaplewski, L. G.; Logan, A.; Macdonald, R.; MacLeod, L.; Peasley, H.; Mitchell, J. P.; Nayal, N.; Yadav, A.; Srivastava, A.; Haydon, D. J., An Improved Small-Molecule Inhibitor of FtsZ with Superior In Vitro Potency, Drug-Like Properties, and In Vivo Efficacy, *Antimicrob. Agents Chemother.* 2013, 57 (1), 317-325.

[11] Matsui, T.; Yamane, J.; Mogi, N.; Yamaguchi, H.; Takemoto, H.; Yao, M.; Tanaka, I., Structural reorganization of the bacterial cell-division protein FtsZ from *Staphylococcus aureus*. *Acta Cryst. D* 2012, 68, 1175-1188.

[12] Tan, C. M.; Therien, A. G.; Lu, J.; Lee, S. H.; Caron, A.; Gill, C. J.; Lebeau-Jacob, C.; Benton-Perdomo, L.; Monteiro, J. M.; Pereira, P. M.; Elsen, N. L.; Wu, J.; Deschamps, K.; Petcu, M.; Wong, S.; Daigneault, E.; Kramer, S.; Liang, L. Z.; Maxwell, E.; Claveau, D.; Vaillancourt, J.; Skorey, K.; Tam, J.; Wang, H.; Meredith, T. C.; Sillaots, S.; Wang-Jarantow, L.; Ramtohul, Y.; Langlois, E.; Landry, F.; Reid, J. C.; Parthasarathy, G.; Sharma, S.; Baryshnikova, A.; Lumb, K. J.; Pinho, M. G.; Soisson, S. M.; Roemer, T., Restoring Methicillin-Resistant *Staphylococcus aureus* Susceptibility to beta-Lactam Antibiotics. *Sci. Transl. Med.* 2012, 4 (126), 126ra35.

[13] Kaul, M.; Parhi, A. K.; Zhang, Y.; LaVoie, E. J.; Tuske, S.; Arnold, E.; Kerrigan, J. E.; Pilch, D. S., A Bactericidal Guanidinomethyl Biaryl That Alters the Dynamics of Bacterial FtsZ Polymerization. *J. Med. Chem.* 2012, 55, 10160-10176.

[14] Plaza, A.; Keffer, J. L.; Bifulco, G.; Lloyd, J. R.; Bewley, C. A., Chrysophaentins A-H, Antibacterial Bisdiarylbutene Macrocycles That Inhibit the Bacterial Cell Division Protein FtsZ. *J. Am. Chem. Soc.* 2010, 132 (26), 9069-9077.

[15] (a) Marcelo, F.; Huecas, S.; Ruiz-Ávila, L. B.; Cañada, F. J.; Perona, A.; Poveda, A.; Martín-Santamaría S.; Morreale, A.; Jiménez-Barbero, J.; Andreu, J. M., Interactions of Bacterial Cell Division Protein FtsZ with C8-Substituted Guanine Nucleotide Inhibitors. A Combined NMR, Biochemical and Molecular Modeling Perspective. *J. Am. Chem. Soc.* 2013, 135 (44), 16418-16428; (b) Huecas, S.; Marcelo, F.; Perona A.; Ruiz-Avila, L. B.; Morreale, A.; Canada, F. J.; Jimenez-Barbero, J.; Andreu, J. M., Beyond a Fluorescent Probe: Inhibition of Cell Division Protein FtsZ by mant-GTP Elucidated by NMR and Biochemical Approaches. *ACS Chem. Biol.* 2015, 10 (10), 2382-2392.

[16] (a) Sun, N.; Chan, F.-Y.; Lu, Y.-J.; Neves, M. A. C.; Lui, H.-K.; Wang, Y.; Chow, K.-Y.; Chan, K.-F.; Yan, S.-C.; Leung, Y.-C.; Abagyan, R.; Chan, T.-H.; Wong. K.-Y., Rational Design of Berberine-Based. FtsZ inhibitors with Broad-Spectrum Antibacterial Activity. *PLoS ONE* 2014, 9 (5), e97514; (b) Domadia, P. N.; Bhunia, A.; Sivaraman, J.; Swamp, S.; Dasgupta, D., Berberine targets assembly of *Escherichia coli* cell division protein FtsZ. *Biochemistry* 2008, 47 (10), 3225-3234.

[17] (a) Artola, M.; Ruiz-Avila, L. B.; Vergoñós, A.; Huecas, S.; Araujo-Bazán, L.; Martín-Fontecha, M.; Vázquez-Villa, H.; Turrado, C.; Ramírez-Aportela, E.; Hoegl, A.; Nodwell, M.; Barasoain, I.; Chacón, P.; Sieber, S. A.; Andrew, J. M.; López-Rodríguez, M. L., Effective GTP-Replacing FtsZ Inhibitors and Antibacterial Mechanism of Action. *ACS Chem. Biol.* 2015, 10 (3), 834-843; (b) Ruiz-Avila, L. B.; Huecas, S.; Artola, M.; Vergoñás, A.; Ramírez-Aportela, E.; Cercenado, E.; Barasoain, I.; Vázquez-Villa, H.; Martín-Fontecha, M.; Chacón, P.; López-Rodríguez, M. L.; Andreu, J. M., Synthetic Inhibitors of Bacterial Cell Division Targeting the GTP-Binding Site of FtsZ. *ACS Chem. Biol.* 2013, 8 (9), 2072-2083.

[18] Chan, F. Y.; Sun, N.; Neves, M. A. C.; Lam, P. C. H.; Chung, W. H.; Wong, L. K.; Chow, H. Y.; Ma, D. L.; Chan, P. H.; Leung, Y. C.; Chan, T. H.; Abagyan, R.; Wong, K. Y., Identification of a New Class of FtsZ Inhibitors by Structure-Based Design and in Vitro Screening. *J. Chem. Inf. Model.* 2013, 53 (8), 2131-2140.

[19] Chan, F. Y.; Sun, N.; Leung, Y. C.; Wong, K. Y., Antimicrobial activity of a quinuclidine-based FtsZ inhibitor and its synergistic potential with beta-lactam antibiotics. *J. Antibiot.* 2015, 68 (4), 253-258.

[20] Karpov, A. S.; Muller, T. J. J., Straightforward novel one-pot enaminone and pyrimidine syntheses by coupling-addition-cyclocondensation sequences. *Synthesis* 2003, (18), 2815-2826.

[21] Clinical and Laboratory Standards Institute. Methods for Dilution Antimicrobial Susceptibility Tests for Bacteria That Grow Aerobically; Approved Standard, 7th ed.; CLSI document M07-A7; Clinical and Laboratory Standards Institute: Wayne, Pa., 2006.

[22] Tsai, C. J.-Y.; Loh, J. M. S.; Proft, T., *Galleria mellonella* infection models for the study of bacterial diseases and for antimicrobial drug testing. *Virulence* 2016, 7, 214-229.

[23] Mayer, M.; Meyer, B., Characterization of Ligand Binding by Saturation Transfer Difference NMR Spectroscopy. *Angew. Chem. Int. Ed.* 1999, 38, 1784-1788.

[24] Lam, T.; Hilgers, M. T.; Cunningham, M. L.; Kwan, B. P.; Nelson, K. J.; Brown-Driver, V.; Ong, V.; Trzoss, M.; Hough, G.; Shaw, K. J.; Finn, J., Structure-Based Design of New Dihydrofolate Reductase Antibacterial Agents: 7-(Benzimidazol-1-yl)-2,4-diaminoquinazolines. *J. Med. Chem.* 2014, 57, 651-668.

What is claimed is:

1. A pyrimidine having the structure of formula (I):

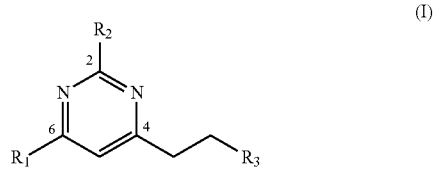

wherein R$_1$ represents alkyl having 1-10 carbon atoms, aryl having one or two 6-membered aromatic rings, or heteroaryl having one or two 6-membered aromatic rings with at least one nitrogen (N) as the heteroatom;

R$_2$ represents an aryl or heteroaryl group; and

R$_3$ represents

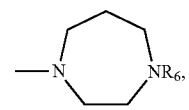

Wherein R$_6$ is selected from the group consisting of alkyl having 1-10 carbon atoms, optionally substituted benzyl, optionally substituted phenyl, pyridylmethyl, optionally substituted benzoyl, optionally substituted phenethyl, piperonyl, 3-phenyl-2-propen-1-yl, optionally substituted cinnamoyl, alkyl sulphonyl, aryl sulphonyl and heteroaryl sulphonyl.

2. The pyrimidine of claim 1, wherein R$_1$ is selected from the group consisting of alkyl having 1-8 carbon atoms, phenyl and substituted phenyl.

3. The pyrimidine of claim 1, wherein $R_1$ is selected from the group consisting of phenyl, 3-pentyl and n-pentyl.

4. The pyrimidine of claim 1, wherein $R_2$ is selected from the group consisting of phenyl, substituted phenyl, pyridin-2-yl, pyridin-3-yl and pyridin-4-yl.

5. The pyrimidine of claim 1, wherein $R_6$ is selected from the group consisting of 4-iso-propylbenzyl, 4-tert-butylbenzyl, 4-bromobenzyl, 3-fluorobenzyl, 3,4-difluorobenzyl, 4-chlorobenzyl, 4-(trifluoromethyl)benzyl, 2-(trifluoromethyl)benzyl, 3-(trifluoromethyl)benzyl, and 4-(trifluoromethyl) phenethyl.

6. The pyrimidine of claim 1, selected from the group consisting of:

1-(2-(6-phenyl-2-(pyridin-4-yl)pyrimidin-4-yl)ethyl)-4-(4-(trifluoromethyl)benzyl)-1,4-diazepane;

1-(4-isopropylbenzyl)-4-(2-(6-phenyl-2-(pyridin-4-yl)pyrimidin-4-yl)ethyl)-1,4-diazepane;

1-(2-(6-phenyl-2-(pyridin-4-yl)pyrimidin-4-yl)ethyl)-4-(4-(trifluoromethyl)phenethyl)-1,4-diazepane;

1-(4-(tert-butyl)benzyl)-4-(2-(6-phenyl-2-(pyridin-4-yl)pyrimidin-4-yl)ethyl)-1,4-diazepane;

1-(4-bromobenzyl)-4-(2-(6-phenyl-2-(pyridin-4-yl)pyrimidin-4-yl)ethyl)-1,4-diazepane;

1-(2-(6-(pentan-3-yl)-2-(pyridin-4-yl)pyrimidin-4-yl)ethyl)-4-(4-(trifluoromethyl)benzyl)-1,4-diazepane; and 1-(2-(6-(pentan-3-yl)-2-(pyridin-4-yl)pyrimidin-4-yl)ethyl)-4-(4-(trifluoromethyl)phenethyl)-1,4-diazepane.

7. The pyrimidine of claim 1, selected from the group consisting of:

1-(4-isopropylbenzyl)-4-(2-(6-pentyl-2-(pyridin-4-yl)pyrimidin-4-yl)ethyl)-1,4-diazepane;

1-(2-(6-pentyl-2-(pyridin-4-yl)pyrimidin-4-yl)ethyl)-4-(3-(trifluoromethyl)benthyl)-1,4-diazepane;

1-(2-(6-phenyl-2-(pyridin-4-yl)pyrimidin-4-yl)ethyl)-4-(3,4-difluorobenzyl)-1,4-diazepane;

1-(2-(6-phenyl-2-(pyridin-4-yl)pyrimidin-4-yl)ethyl)-4-(3-fluorobenzyl)-1,4-diazepane;

1-(2-(6-phenyl-2-(pyridin-4-yl)pyrimidin-4-yl)ethyl)-4-(4-chlorobenzyl)-1,4-diazepane;

1-(4-isopropylbenzyl)-4-(2-(6-(pentan-3-yl)-2-(pyridin-4-yl)pyrimidin-4-yl)ethyl)-1,4-diazepane;

1-(4-(tert-butyl)benzyl)-4-(2-(6-(penta-3-yl)-2-(pyridin-4-yl)pyrimidin-4-yl)ethyl)-1,4-diazepane;

1-(4-bromobenzyl)-4-(2-(6-(pentan-3-yl)-2-(pyridin-4-yl)pyrimidin-4-yl)ethyl)-1,4-diazepane;

1-(2-(6-(pentan-3-yl)-2-(pyridin-4-yl)pyrimidin-4-yl)ethyl)-4-(3-(trifluoromethyl)benthyl)-1,4-diazepane; and 1-(2-(6-(pentan-3-yl)-2-(pyridin-4-yl)pyrimidin-4-yl)ethyl)-4-(2-(trifluoromethyl)benthyl)-1,4-diazepane.

8. A composition comprising the pyrimidine of claim 1 or its pharmaceutically acceptable salt, and a pharmaceutically acceptable carrier.

9. A method for treating a bacterial infection in a subject, comprising the step of administering to the subject in need thereof a therapeutically effective amount of a composition comprising a pyrimidine or its pharmaceutically acceptable salt, and a pharmaceutically acceptable carrier, wherein said pyrimidine has the structure of formula (I):

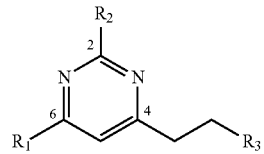

wherein $R_1$ represents alkyl having 1-10 carbon atoms, aryl having one or two 6-membered aromatic rings, or heteroaryl having one or two 6-membered aromatic rings with at least one nitrogen (N) as the heteroatom;

$R_2$ represents an aryl or heteroaryl group; and $R_3$ represents

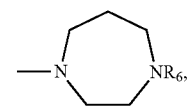

Wherein $R_6$ is selected from the group consisting of alkyl having 1-10 carbon atoms, optionally substituted benzyl, optionally substituted phenyl, pyridylmethyl, optionally substituted benzoyl, optionally substituted phenethyl, piperonyl, 3-phenyl-2-propen-1-yl, optionally substituted cinnamoyl, alkyl sulphonyl, aryl sulphonyl and heteroaryl sulphonyl;

and wherein said infection is caused by bacteria selected from the group consisting of *Staphylococcus aureus*, Methicillin-resistant *Staphylococcus aureus* (MRSA), *Enterococcus faecalis, Bacillus subtilis, Propionibacterium acnes*, and *Clostridium difficile*.

10. The method of claim 9, wherein $R_1$ is selected from the group consisting of alkyl having 1-8 carbon atoms, phenyl and substituted phenyl.

11. The method of claim 9, wherein $R_2$ is selected from the group consisting of phenyl, substituted phenyl, pyridin-2-yl, pyridin-3-yl and pyridin-4-yl.

12. The method of claim 9, wherein the pyrimidine is selected from the group consisting of:

1-(2-(6-phenyl-2-(pyridin-4-yl)pyrimidin-4-yl)ethyl)-4-(4-(trifluoromethyl)benzyl)-1,4-diazepane;

1-(4-isopropylbenzyl)-4-(2-(6-phenyl-2-(pyridin-4-yl)pyrimidin-4-yl)ethyl)-1,4-diazepane;

1-(2-(6-phenyl-2-(pyridin-4-yl)pyrimidin-4-yl)ethyl)-4-(4-(trifluoromethyl)phenethyl)-1,4-diazepane;

1-(4-(tert-butyl)benzyl)-4-(2-(6-phenyl-2-(pyridin-4-yl)pyrimidin-4-yl)ethyl)-1,4-diazepane;

1-(4-bromobenzyl)-4-(2-(6-phenyl-2-(pyridin-4-yl)pyrimidin-4-yl)ethyl)-1,4-diazepane;

1-(2-(6-(pentan-3-yl)-2-(pyridin-4-yl)pyrimidin-4-yl)ethyl)-4-(4-(trifluoromethyl)benzyl)-1,4-diazepane; and 1-(2-(6-(pentan-3-yl)-2-(pyridin-4-yl)pyrimidin-4-yl)ethyl)-4-(4-(trifluoromethyl)phenethyl)-1,4-diazepane.

13. The method of claim 9, wherein the pyrimidine is selected from the group consisting of:

1-(4-isopropylbenzyl)-4-(2-(6-pentyl-2-(pyridin-4-yl)pyrimidin-4-yl)ethyl)-1,4-diazepane;

1-(2-(6-pentyl-2-(pyridin-4-yl)pyrimidin-4-yl)ethyl)-4-(3-(trifluoromethyl)benthyl)-1,4-diazepane;

1-(2-(6-phenyl-2-(pyridin-4-yl)pyrimidin-4-yl)ethyl)-4-(3,4-difluorobenzyl)-1,4-diazepane;

1-(2-(6-phenyl-2-(pyridin-4-yl)pyrimidin-4-yl)ethyl)-4-(3-fluorobenzyl)-1,4-diazepane;

1-(2-(6-phenyl-2-(pyridin-4-yl)pyrimidin-4-yl)ethyl)-4-(4-chlorobenzyl)-1,4-diazepane;

1-(4-isopropylbenzyl)-4-(2-(6-(pentan-3-yl)-2-(pyridin-4-yl)pyrimidin-4-yl)ethyl)-1,4-diazepane;

1-(4-(tert-butyl)benzyl)-4-(2-(6-(penta-3-yl)-2-(pyridin-4-yl)pyrimidin-4-yl)ethyl)-1,4-diazepane;

1-(4-bromobenzyl)-4-(2-(6-(pentan-3-yl)-2-(pyridin-4-yl)pyrimidin-4-yl)ethyl)-1,4-diazepane;

1-(2-(6-(pentan-3-yl)-2-(pyridin-4-yl)pyrimidin-4-yl)ethyl)-4-(3-(trifluoromethyl)benthyl)-1,4-diazepane; and 1-(2-(6-(pentan-3-yl)-2-(pyridin-4-yl)pyrimidin-4-yl)ethyl)-4-(2-(trifluoromethyl)benthyl)-1,4-diazepane.

14. The method of claim 9, wherein the infection is a skin infection, a gastrointestinal infection, a respiratory infection, a urinary tract infection, or a reproductive bacterial cell infection.

15. The method of claim 9, wherein the pyrimidine inhibits bacterial cell division.

16. The method of claim 9, wherein the pyrimidine inhibits Z-ring formation by filamenting temperature-sensitive mutant Z (FtsZ) protein within a bacterial cell.

17. The method of claim 9, wherein the pyrimidine binds to the guanosine triphosphate (GTP) binding site of FtsZ within a bacterial cell.

18. The method of claim 9, wherein the subject is a vertebrate, a mammal or human.

19. The method of claim 9, wherein the composition is administered orally, nasally, aurally, ocularly, sublingually, buccally, systemically, transdermally, mucosally, via cerebral spinal fluid injection, vein injection, muscle injection, peritoneal injection, subcutaneous injection, or by inhalation.

20. The method of claim 9, wherein the composition is formulated in the form of a cream, gel, ointment, suppository, tablet, granule, injection, powder, solution, suspension, spray, patch or capsule.

* * * * *